United States Patent
Renz et al.

(10) Patent No.: US 7,666,162 B2
(45) Date of Patent: Feb. 23, 2010

(54) BREAST CUP

(75) Inventors: Charles J Renz, Briarcliff Manor, NY (US); David Robson, Riverside, RI (US); Marco Wo, Providence, RI (US); Christopher Kampf, Cranston, RI (US); Aidan Petrie, Jamestown, RI (US); Michael Pereira, Smithfield, RI (US)

(73) Assignee: Playtex Products, Inc., Westport, CT (US)

( * ) Notice: Subject to any disclaimer, the term of this patent is extended or adjusted under 35 U.S.C. 154(b) by 514 days.

(21) Appl. No.: 10/331,183

(22) Filed: Dec. 27, 2002

(65) Prior Publication Data

US 2003/0149398 A1 Aug. 7, 2003

Related U.S. Application Data

(60) Provisional application No. 60/343,769, filed on Dec. 27, 2001, provisional application No. 60/403,415, filed on Aug. 14, 2002, provisional application No. 60/428,463, filed on Nov. 22, 2002.

(51) Int. Cl.
*A61M 1/06* (2006.01)
(52) U.S. Cl. .................................................. 604/74
(58) Field of Classification Search ............ 604/74–76; 119/14.47, 14.49
See application file for complete search history.

(56) References Cited

U.S. PATENT DOCUMENTS

| | | | | |
|---|---|---|---|---|
| 11,135 A | 6/1854 | Needham | | |
| 2,160,651 A | 5/1939 | Erling | ............... | 31/69 |
| 2,419,795 A | 4/1947 | Saunders | ............... | 128/297 |
| 2,542,505 A | 2/1951 | Gascoigne | ............... | 128/281 |
| 2,584,435 A | 2/1952 | Doerr | ............... | 257/10 |
| 2,612,136 A | 9/1952 | Davis | ............... | 119/14.52 |
| 2,696,193 A | 12/1954 | Domingo | ............... | 119/14.01 |
| 2,809,607 A | 10/1957 | Golay | ............... | 119/14.41 |
| 3,382,867 A | 5/1968 | Reaves | ............... | 128/38 |
| 3,620,408 A | 11/1971 | Holbrook et al. | ............... | 220/60 |
| 3,699,815 A | 10/1972 | Holbrook | ............... | 73/427 |
| 3,738,363 A | 6/1973 | Lunas et al. | ............... | 128/281 |
| 3,741,161 A | 6/1973 | Zhuk et al. | ............... | 119/14.36 |
| 3,911,920 A | 10/1975 | Susinn | ............... | 128/281 |
| 3,977,405 A | 8/1976 | Yanase | ............... | 128/281 |
| 4,041,904 A | 8/1977 | Yang | ............... | 119/14.41 |
| D251,015 S | 2/1979 | Cone | ............... | D24/23 |
| 4,249,481 A | 2/1981 | Adams | ............... | 119/14.02 |
| 4,263,912 A | 4/1981 | Adams | ............... | 128/281 |
| 4,280,445 A | 7/1981 | Phillips | ............... | 119/14.02 |
| 4,311,141 A | 1/1982 | Diamond | ............... | 128/281 |
| 4,323,067 A | 4/1982 | Adams | ............... | 128/281 |
| 4,501,585 A | 2/1985 | Friedman | ............... | 604/346 |

(Continued)

FOREIGN PATENT DOCUMENTS

WO   WO 99/44650   9/1999

*Primary Examiner*—Kevin C Sirmons
*Assistant Examiner*—Catherine N Witczak
(74) *Attorney, Agent, or Firm*—Ohlandt, Greeley, Ruggiero & Perle, L.L.P.

(57) ABSTRACT

A breast cup for use with a breast pump for expressing breast milk is provided. The breast cup sealingly separates the air flow from the breast milk, provides a barrier against impingement of the flexible insert by the user's breast and provides a massaging member for facilitating expression of the breast milk.

43 Claims, 18 Drawing Sheets

U.S. PATENT DOCUMENTS

| | | | |
|---|---|---|---|
| 4,573,969 A | 3/1986 | Schlensog et al. | 604/74 |
| 4,583,668 A * | 4/1986 | Maynard, Jr. | 222/529 |
| 4,583,970 A | 4/1986 | Kirchner | 604/74 |
| D283,732 S | 5/1986 | Elliott | D24/23 |
| 4,607,596 A | 8/1986 | Whittlestone et al. | 119/14.02 |
| 4,673,388 A | 6/1987 | Schlensog et al. | 604/74 |
| 4,680,028 A | 7/1987 | Stuart | 604/74 |
| 4,740,196 A | 4/1988 | Powell | 604/75 |
| 4,754,776 A | 7/1988 | McKee | 137/102 |
| 4,759,747 A | 7/1988 | Aida et al. | 604/74 |
| 4,761,160 A | 8/1988 | Vermillion | 604/76 |
| 4,772,262 A | 9/1988 | Grant et al. | 604/74 |
| 4,774,874 A | 10/1988 | Adahan | 92/59 |
| 4,796,758 A | 1/1989 | Hauk | 206/545 |
| 4,799,922 A | 1/1989 | Beer et al. | 604/74 |
| 4,813,932 A | 3/1989 | Hobbs | 604/74 |
| 4,857,051 A * | 8/1989 | Larsson | 604/74 |
| 4,883,464 A | 11/1989 | Morifuki | 604/74 |
| 4,886,494 A | 12/1989 | Morifuji | 604/74 |
| 4,892,517 A | 1/1990 | Yuan et al. | 604/74 |
| 4,929,229 A | 5/1990 | Larsson | 604/74 |
| D309,500 S | 7/1990 | Yuan et al. | D24/51 |
| 4,950,236 A | 8/1990 | Wilson | 604/74 |
| 4,961,726 A | 10/1990 | Richter | 604/74 |
| 4,964,851 A | 10/1990 | Larsson | 604/74 |
| D313,103 S | 12/1990 | Kawano | D24/51 |
| 5,007,899 A | 4/1991 | Larsson | 604/74 |
| 5,009,638 A | 4/1991 | Riedweg et al. | 604/74 |
| 5,049,126 A | 9/1991 | Larsson | 604/74 |
| 5,071,403 A | 12/1991 | Larsson | 604/74 |
| 5,100,406 A | 3/1992 | Panchula | 606/74 |
| 5,161,482 A | 11/1992 | Griffin | 119/14.02 |
| 5,178,095 A | 1/1993 | Mein | 119/14.47 |
| D345,209 S | 3/1994 | Shoda et al. | D24/109 |
| 5,295,957 A | 3/1994 | Aida et al. | 604/74 |
| 5,304,129 A | 4/1994 | Forgach | 604/74 |
| 5,308,321 A | 5/1994 | Castro | 604/74 |
| 5,358,476 A | 10/1994 | Wilson | 604/74 |
| 5,415,632 A | 5/1995 | Samson | 604/74 |
| 5,474,193 A | 12/1995 | Larsson et al. | 215/11.4 |
| 5,484,202 A * | 1/1996 | Gourley et al. | 366/120 |
| 5,514,166 A | 5/1996 | Silver et al. | 604/74 |
| D372,975 S | 8/1996 | Meyers et al. | D24/109 |
| 5,542,921 A | 8/1996 | Meyers et al. | 604/74 |
| D375,357 S | 11/1996 | Silver | D24/129 |
| 5,571,084 A | 11/1996 | Palmer | 604/74 |
| 5,575,768 A | 11/1996 | Lockridge et al. | 604/74 |
| 5,601,531 A | 2/1997 | Silver | 604/74 |
| 5,616,125 A | 4/1997 | Jelks | 604/74 |
| D383,536 S | 9/1997 | Bachman et al. | D24/109 |
| 5,720,722 A | 2/1998 | Lockridge | 604/74 |
| 5,749,850 A | 5/1998 | Williams et al. | 604/74 |
| 5,776,098 A | 7/1998 | Silver et al. | 604/74 |
| 5,797,875 A | 8/1998 | Silver | 604/74 |
| 5,810,772 A | 9/1998 | Niederberger | 604/74 |
| 5,843,029 A | 12/1998 | Bachman et al. | 604/74 |
| 5,871,456 A | 2/1999 | Armstrong et al. | 601/14 |
| 5,885,246 A * | 3/1999 | Ford | 604/74 |
| D408,528 S | 4/1999 | Kan | D24/109 |
| 5,897,580 A | 4/1999 | Silver | 607/108 |
| 5,902,267 A | 5/1999 | Medo | 604/74 |
| 5,941,847 A | 8/1999 | Huber et al. | 604/74 |
| 5,947,923 A | 9/1999 | Uehara et al. | 604/74 |
| 5,954,690 A | 9/1999 | Larsson | 604/74 |
| 5,971,952 A | 10/1999 | Medo | 604/74 |
| 5,992,347 A | 11/1999 | Innings et al. | 119/14.07 |
| 6,004,186 A | 12/1999 | Penny | 450/36 |
| 6,004,288 A | 12/1999 | Hochstedler et al. | 604/74 |
| D418,598 S | 1/2000 | Jauch | D24/109 |
| D420,443 S | 2/2000 | Morifuji | D24/109 |
| 6,039,001 A * | 3/2000 | Sanford | 119/14.47 |
| 6,042,560 A | 3/2000 | Niederberger | 604/74 |
| 6,045,529 A | 4/2000 | Nüesch | 604/74 |
| 6,050,432 A | 4/2000 | Koehnke | 215/11.3 |
| 6,056,730 A | 5/2000 | Greter | 604/319 |
| 6,090,065 A | 7/2000 | Giles | 604/74 |
| 6,093,168 A | 7/2000 | Mendenhall | 604/74 |
| 6,109,100 A | 8/2000 | Buckley et al. | 73/198 |
| 6,110,140 A | 8/2000 | Silver | 604/74 |
| 6,110,141 A | 8/2000 | Nüesch | 604/74 |
| 6,139,521 A | 10/2000 | Larsson | 604/74 |
| 6,149,395 A | 11/2000 | Richter | 417/182 |
| 6,152,896 A | 11/2000 | Bachman et al. | 604/74 |
| 6,210,360 B1 | 4/2001 | Kong | 604/73 |
| 6,213,840 B1 | 4/2001 | Han | 450/36 |
| 6,227,936 B1 | 5/2001 | Mendoza | 450/36 |
| 6,257,847 B1 | 7/2001 | Silver et al. | 417/415 |
| D446,300 S | 8/2001 | Kirchner | D24/109 |
| D446,852 S | 8/2001 | Johansen et al. | D24/109 |
| D446,853 S | 8/2001 | Johansen et al. | D24/109 |
| 6,270,474 B1 | 8/2001 | Nüesch | 604/74 |
| 6,273,868 B1 | 8/2001 | Nordvik | 604/74 |
| 6,287,521 B1 | 9/2001 | Quay et al. | 422/101 |
| 6,290,671 B1 | 9/2001 | Niederberger | 604/74 |
| 6,299,594 B1 | 10/2001 | Silver | 604/74 |
| 6,328,082 B1 | 12/2001 | Lafond | 141/313 |
| 6,355,012 B1 | 3/2002 | Nüesch | 604/74 |
| 6,358,226 B1 | 3/2002 | Ryan | 604/74 |
| 6,379,327 B2 | 4/2002 | Lundy | 604/74 |
| 6,383,163 B1 | 5/2002 | Kelly et al. | 604/74 |
| 6,383,164 B1 | 5/2002 | Johansen et al. | 604/74 |
| 6,387,072 B1 | 5/2002 | Larsson et al. | 604/74 |
| 6,423,030 B1 | 7/2002 | Silver | 604/74 |
| 6,440,100 B1 | 8/2002 | Prentiss | 604/74 |
| 6,461,324 B1 * | 10/2002 | Schlensog | 604/74 |
| 6,481,986 B1 | 11/2002 | Silver et al. | 417/441 |
| 6,497,677 B2 | 12/2002 | Silver | 604/74 |
| 6,500,143 B2 | 12/2002 | Suh | 604/73 |
| 6,517,513 B1 | 2/2003 | Covington et al. | 604/74 |
| 6,547,756 B1 | 4/2003 | Greter et al. | 604/74 |
| 6,579,258 B1 * | 6/2003 | Atkin et al. | 604/74 |
| 6,585,686 B2 | 7/2003 | Cloud | 604/74 |
| 2001/0016708 A1 | 8/2001 | Kong et al. | 604/152 |
| 2001/0038799 A1 | 11/2001 | Silver et al. | 417/515 |
| 2001/0044593 A1 | 11/2001 | Lundy | 604/74 |
| 2001/0047148 A1 | 11/2001 | Suh | 604/74 |
| 2002/0004642 A1 | 1/2002 | Cloud | 604/74 |
| 2002/0032404 A1 | 3/2002 | Silver | 604/74 |
| 2002/0033199 A1 | 3/2002 | Lafond | 141/10 |
| 2002/0072701 A1 | 6/2002 | Nuesch | 604/74 |
| 2002/0072702 A1 | 6/2002 | Quay | 604/74 |
| 2002/0127580 A1 | 9/2002 | Quay | 435/6 |
| 2002/0156419 A1 | 10/2002 | Silver et al. | 604/74 |
| 2002/0170935 A1 | 11/2002 | Annis | 224/653 |
| 2002/0193731 A1 | 12/2002 | Myers et al. | 604/74 |
| 2002/0198489 A1 | 12/2002 | Silver et al. | 604/74 |
| 2003/0004459 A1 | 1/2003 | McKendry et al. | 604/74 |
| 2003/0040734 A1 | 2/2003 | Morton et al. | 604/514 |
| 2003/0069536 A1 | 4/2003 | Greter et al. | 604/74 |
| 2003/0073951 A1 | 4/2003 | Morton et al. | 604/73 |
| 2003/0150890 A1 | 8/2003 | Perricone | 224/148.6 |
| 2003/0191432 A1 | 10/2003 | Silver | 604/74 |
| 2003/0191433 A1 | 10/2003 | Prentiss | 604/74 |
| 2003/0204164 A1 | 10/2003 | Britto et al. | 604/74 |
| 2004/0015127 A1 * | 1/2004 | Silver et al. | 604/74 |
| 2004/0127845 A1 * | 7/2004 | Renz et al. | 604/74 |

* cited by examiner

BREAST CUP

RELATED APPLICATION

This application is related to and claims priority in, copending U.S. Provisional Application Ser. No. 60/343,769, filed Dec. 27, 2001, copending U.S. Provisional Application Ser. No. 60/403,415, filed Aug. 14, 2002 and copending U.S. Provisional Application Ser. No. 60/428,463, filed Nov. 22, 2002, the disclosures of which are incorporated herein by reference.

BACKGROUND OF THE INVENTION

1. Field of the Invention

The present invention relates to apparatus and methods for obtaining breast milk. More particularly, the present invention relates to a breast cup for expressing breast milk.

2. Description of the Related Art

Breast pump systems using breast cups for obtaining breast milk, both manually and automatically, are known in the art. Conventional breast cups use a vacuum source to generate a negative pressure or vacuum that is transmitted to a breast hood or cup, which is placed on the breast. Typically, such breast cups are disposed remote from the breast pump when in use and the negative pressure or vacuum is transmitted to the breast hood or cup via tubing or conduit.

The conventional devices suffer from the drawback of requiring the vacuum source and the breast milk to be in fluid communication, which can result in breast milk entering the tubing and even worse, entering the breast pump. This results in unwanted clean up, as well as potential damage to the system. Additionally, conventional breast cups suffer from the drawback of failing to apply an adequate massaging action upon the breast to facilitate expression of milk. Such devices often provide a breast hood or cup that impinges upon the nipple resulting in discomfort to the user.

SUMMARY OF THE INVENTION

It is an object of the present invention to provide a breast cup in which the vacuum source and breast are in fluid isolation thereby preventing or ameliorating the possibility of contamination.

It is another object of the present invention to provide such a breast cup that applies both a positive pressure and a negative pressure to a breast to express breast milk.

It is yet another object of the present invention to provide such a breast cup that improves the massage on the areola region of the breast.

These and other objects and advantages of the present invention are provided by a breast cup having a housing, a flexible insert sealingly secured to the housing to form an air volume and a liquid volume, and an air orifice in fluid communication with the air volume and in fluid isolation with the liquid volume. The air volume and the liquid volume are in fluid isolation and the air volume expands or contracts in response to the positive or negative pressures.

The present invention also includes a breast cup having a housing with an air orifice, a flexible insert sealingly secured to the housing to form an air volume and a liquid volume, a holder having a one-way valve and secured to the housing, and a container secured to the holder. The air orifice is in fluid communication with the air volume and in fluid isolation with the liquid volume. The air volume and the liquid volume are in fluid isolation. The air volume expands or contracts in response to the positive or negative pressures to cause a positive or negative pressure in the liquid volume, and the liquid volume is in fluid communication with the container through the one way-valve to permit flow into the container.

The present invention further includes a breast cup having a housing with an air orifice, a flexible insert sealingly secured to the housing to form an air volume and a liquid volume, a holder having a one-way valve with the holder being secured to the housing, and a container secured to the holder. The air orifice is in fluid communication with the air volume and in fluid isolation with the liquid volume, and the air volume and the liquid volume are in fluid isolation. The pressure is applied to the air volume causing the flexible insert to move with respect to the housing, and the liquid volume is in fluid communication with the container. The flexible insert can have a bladder and the air volume can be disposed at least partially in the bladder, and the bladder moves in response to the pressure.

The present invention additionally includes a breast hood having a rigid structure, a flexible structure sealingly secured to the rigid structure, a displacement volume disposed between the rigid structure and the flexible structure, a liquid volume defined by the rigid structure, the flexible structure or both with the liquid volume being in fluid isolation from the pressure source, and a channel in fluid communication with the pressure source and the displacement volume. The pressure source changes the pressure in the displacement volume.

The flexible structure can have a bladder and the displacement volume can be disposed at least partially in the bladder, wherein the bladder moves in response to a change in pressure in the displacement volume. The flexible structure can also have a second portion having a circumferential wall and a plurality of spacers formed in the circumferential wall with the circumferential wall being separated from the rigid structure by the plurality of spacers. The circumferential wall and the plurality of spacers at least partially define the displacement volume, and the circumferential wall is moved in relation to the rigid structure by the change in pressure in the displacement volume.

The flexible insert can comprise a bladder with the air volume being disposed at least partially in the bladder, and the bladder expanding or contracting in response to the positive or negative pressures. The breast cup can also have a barrier member disposed substantially adjacent to the bladder with the barrier member preventing the breast from contacting the bladder. The barrier member can have a cylindrical shape and is disposed in the liquid volume.

The flexible insert can have a funnel shape with a first portion that at least partially defines the air volume and a massaging projection formed on the first portion. The massaging projection can be disposed along the first portion to be in proximity to the areola region of the breast. The massaging projection can have a star-like shape. The flexible insert can have a second portion with a circumferential wall and a plurality of spacers formed in the circumferential wall. The circumferential wall preferably being separated from the housing by the plurality of spacers, and the circumferential wall and the plurality of spacers at least partially defining the air volume. The circumferential wall is moved in proximity to the housing by the negative pressure and the circumferential wall is moved remote from the housing by the positive pressure. The plurality of spacers can be a plurality of pleats formed in the circumferential wall.

The housing can have a first end and a second end and the insert can have a third end and a fourth end. The first end can be removably secured to the second end by a first securing structure, and the third end can be removably secured to the fourth end by a second securing structure. The first securing structure and the second securing structure can be tongue and groove securing structures. The air volume can have a maximum capacity for expansion and the maximum capacity for expansion can be an upper limit for the positive pressure.

The housing, the insert and the holder can be securable to each other at any rotational orientation. The holder can be secured to the housing by a snap fit connection. The container can be a first container having a first diameter and a second container having a second diameter. The holder can have a first securing structure and a second securing structure with the first securing structure being removably securable to the first container and the second securing structure being removably securable to the second container. The first securing structure can be a first threaded surface having a first inner diameter and the second securing structure can be a second threaded surface having a second inner diameter. The first threaded surface and the second threaded can be concentrically disposed on the holder.

The holder can have a channel that is in fluid communication with the liquid volume and the container, and the one-way valve can be operably connected to the channel. The breast cup can further have an indicator that indicates an area for disengagement of the holder from the housing. The indicator can be formed on the holder. The indicator can be an arcuate projection.

BRIEF DESCRIPTION OF THE DRAWINGS

Other and further objects, advantages and features of the present invention will be understood by reference to the following.

DESCRIPTION OF THE INVENTION

Figure 1:
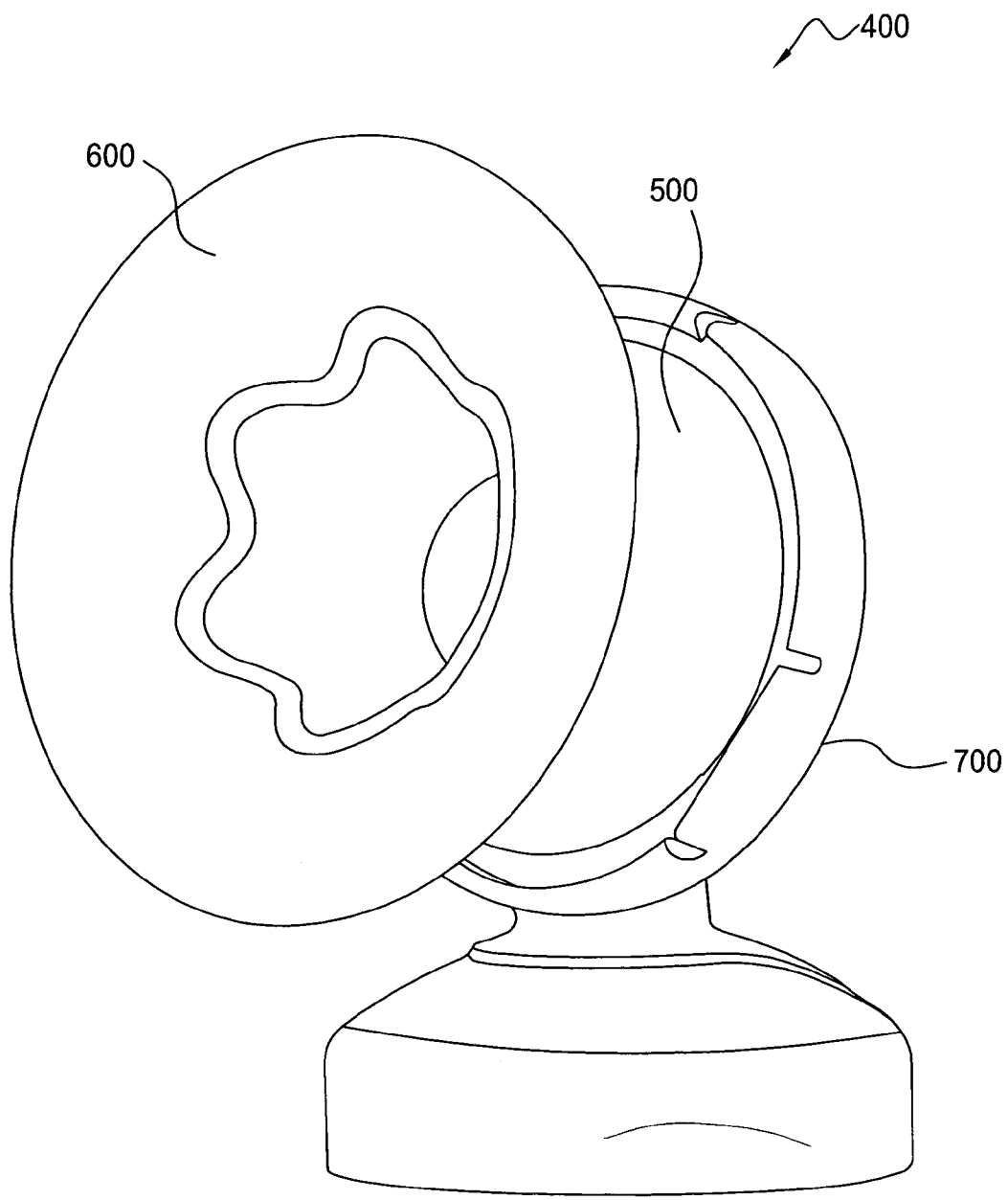
FIG. 1 is a front perspective view of a breast cup of the present invention.
Figure 2:
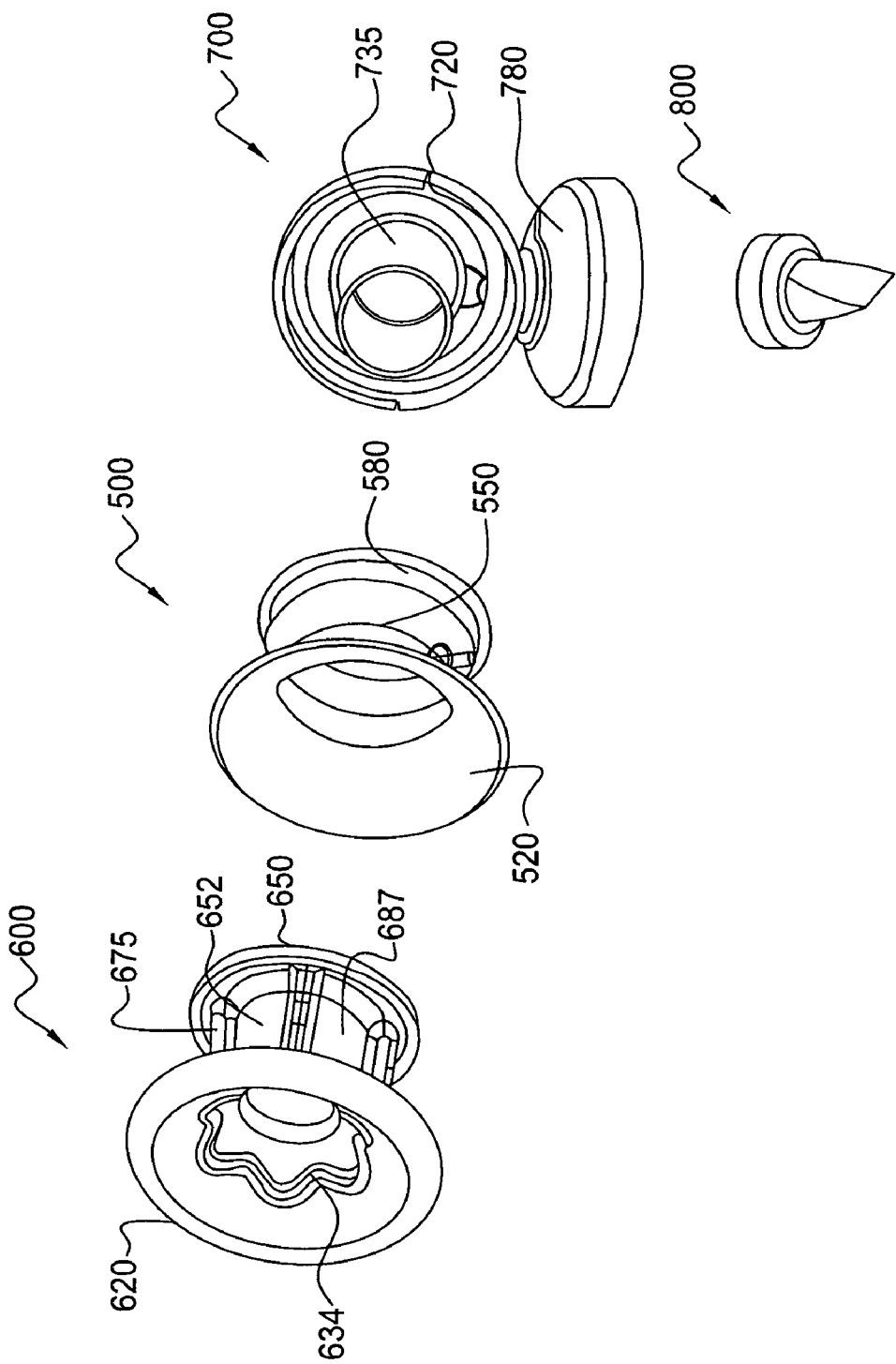
FIG. 2 is an exploded view of the breast cup of FIG. 1.
Figure 3:
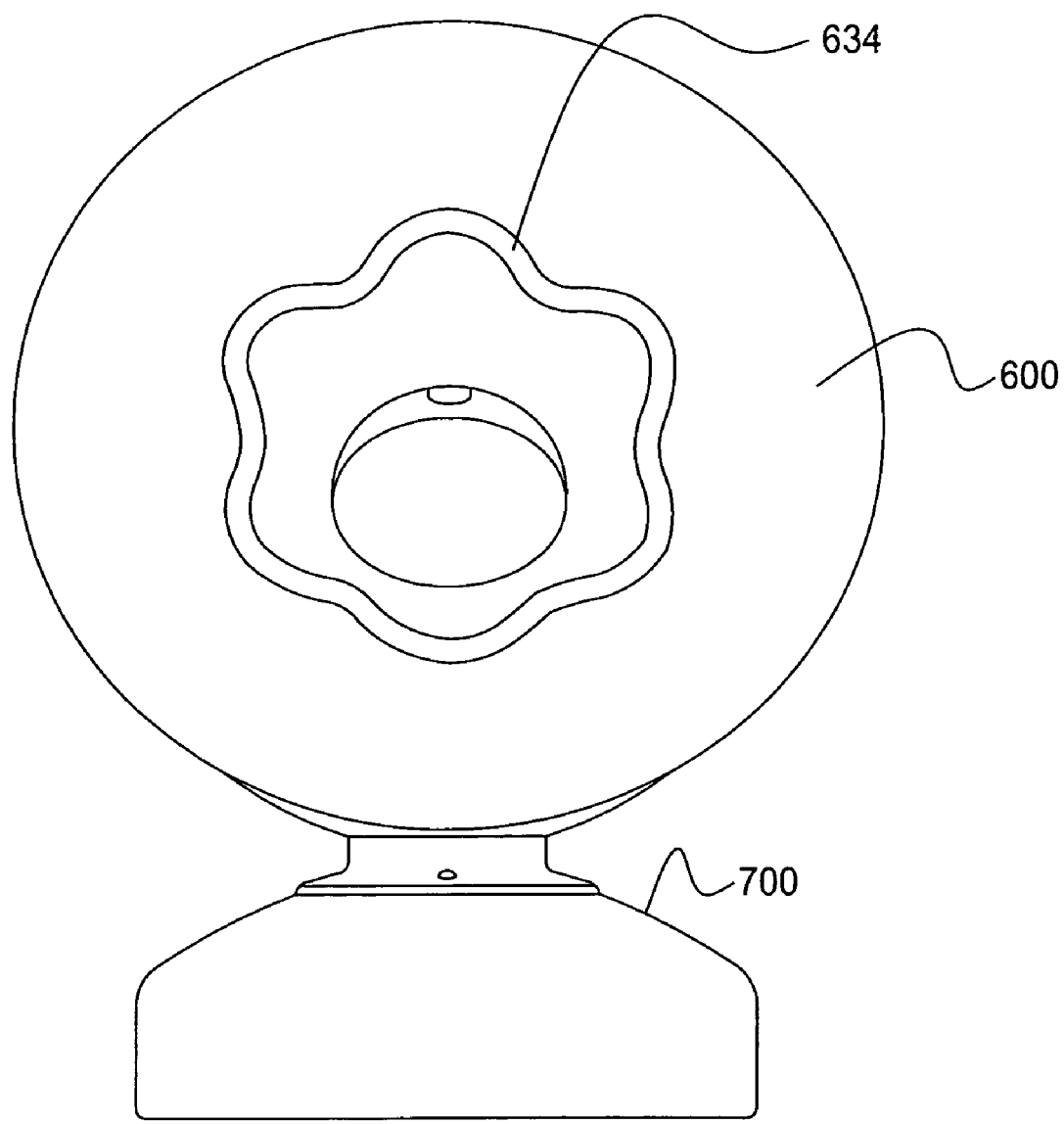
FIG. 3 is a front view of the breast cup of FIG. 1.
Figure 4:
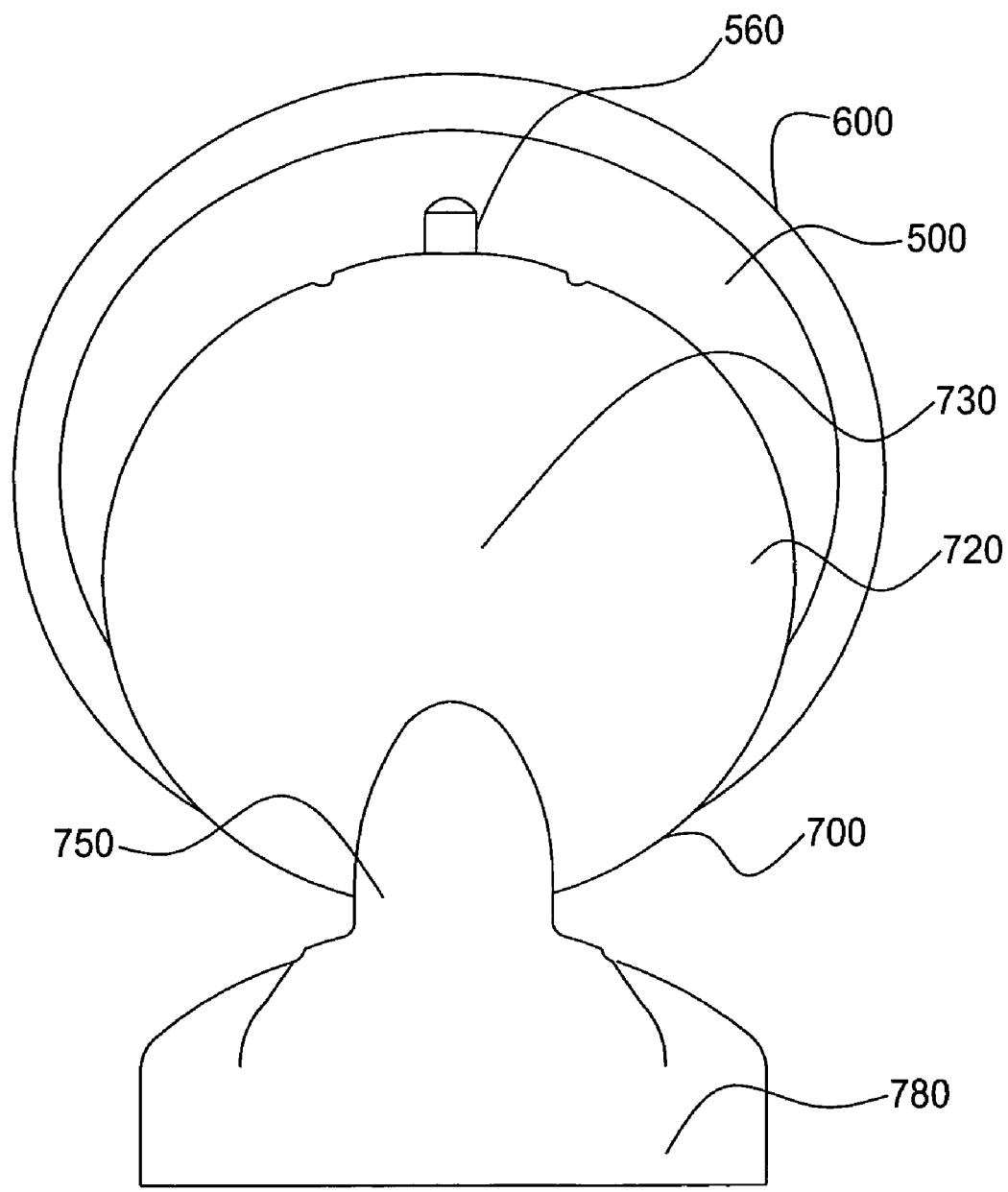
FIG. 4 is a rear view of the breast cup of FIG. 1.
Figure 5:
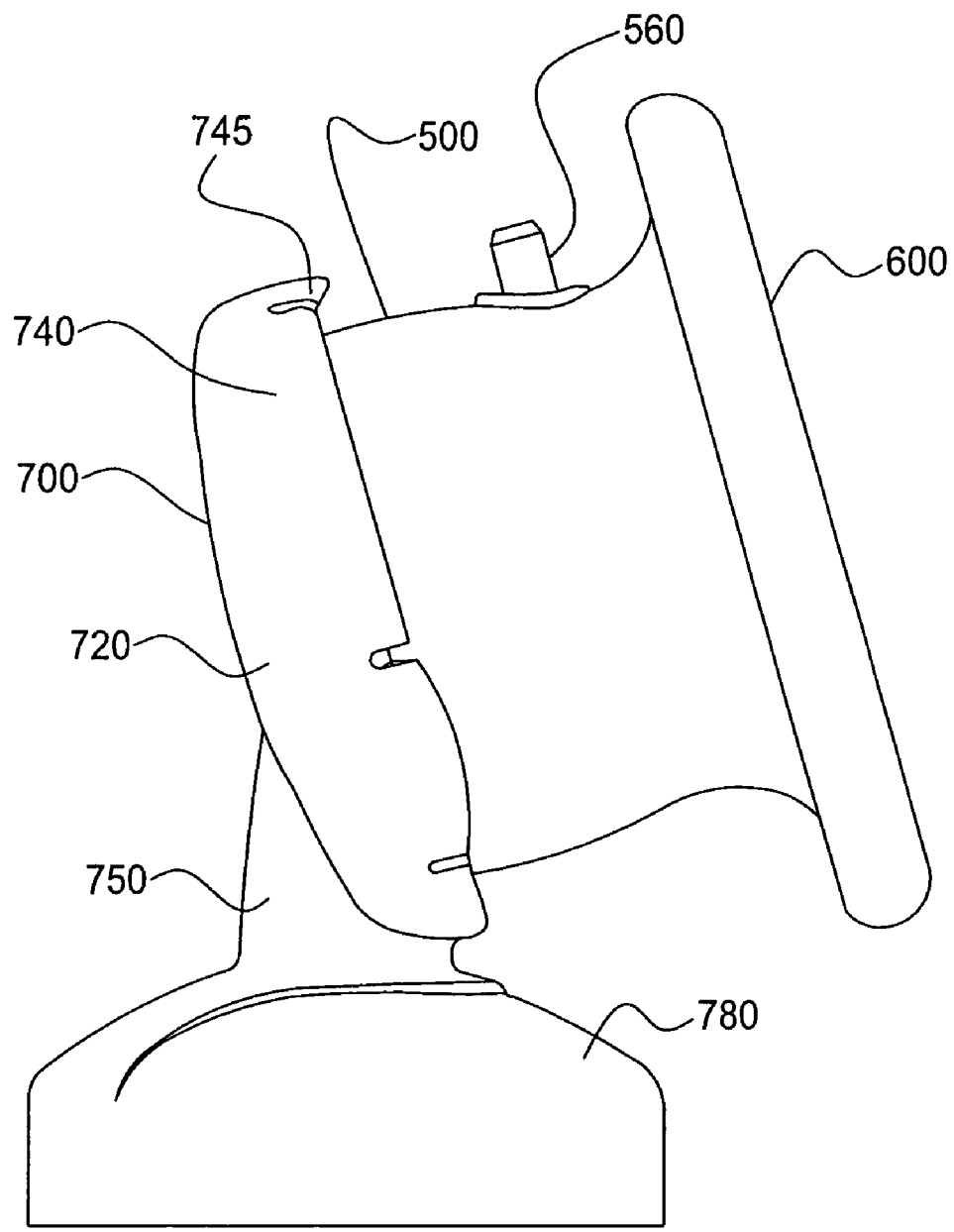
FIG. 5 is a side view of the breast cup of FIG. 1.
Figure 6:
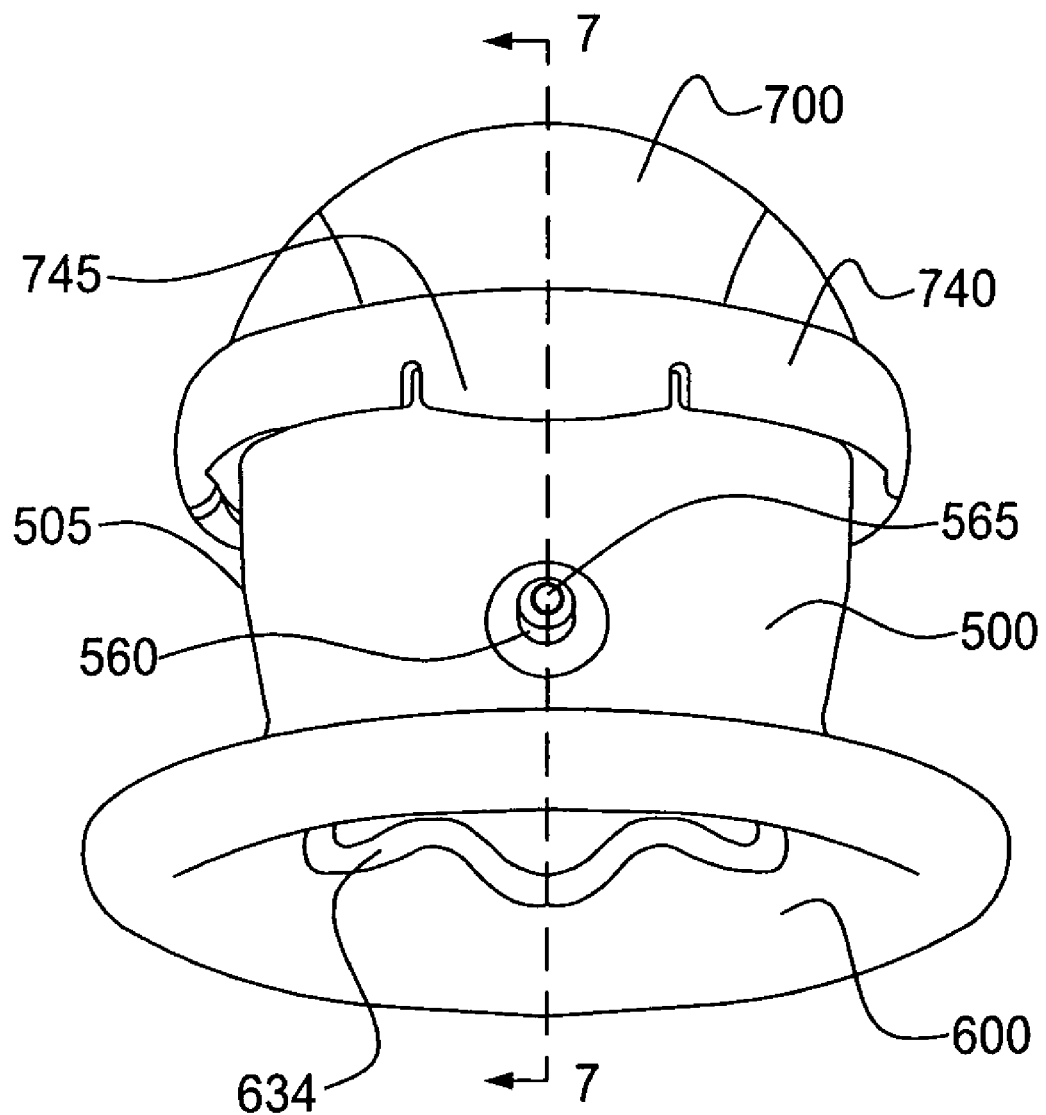
FIG. 6 is a top view of the breast cup of FIG. 1.

Referring to the drawings and, in particular, FIGS. 1 and 2, there is shown a preferred embodiment of a breast cup of the present invention generally represented by reference numeral 400. Breast cup 400 has a housing 500, a flexible insert 600, a holder 700 and a valve 800.

Referring to FIGS. 1 through 8, housing 500 is a rigid structure formed by a circumferential wall 505 defining a housing volume 510. Circumferential wall 505 has a funnel shape with a generally hour-glass-shaped cross-section. Housing 500 has an outer section 520, a middle section 550 and an inner section 580. In this embodiment, outer section 520 generally has a diameter that is larger than the diameters of middle section 550 or inner section 580. Circumferential wall 505 of outer section 520 has a radius of curvature that is smaller than the radius of curvature of the circumferential wall at middle section 550 or inner section 580. Alternative shapes can also be used for breast cup 400. However, the shape of this embodiment provides for a wide or enlarged outer section 520 that facilitates engagement of breast cup 400 with a user's breast.

Outer section 520 has an outer end 525 that is adapted for engagement with insert 600. Outer end 525 preferably has a generally uniform cross-section and uses a tongue and groove connection to engage with insert 600. This type of engagement between outer end 525 and insert 600 allows a user to engage the outer end with the insert at any orientation or alignment to facilitate assembly. However, alternative securing structures can also be used, such as, for example, a projection or number of projections formed on outer end 525 that engage with corresponding grooves or orifices formed in insert 600.

Middle section 550 has an air orifice 560 formed through circumferential wall 505. Preferably, air orifice 560 is a projection extending outwardly from circumferential wall 505 and has a central opening 565 formed therethrough. Central opening 565 provides for fluid communication through air orifice 560 into inner volume 510. Preferably, air orifice 560 has a cylindrical shape and is substantially perpendicular to circumferential wall 505. More preferably, air orifice 560 has a height and diameter that allows for a friction fit with air tubing or conduit. Air orifice 560 can also have a securing structure attached thereto (not shown), such as, for example, a retaining ring or have a shape, such as, for example, inwardly tapered, to facilitate securing of air tubing or conduit with the air orifice.

Figure 7:
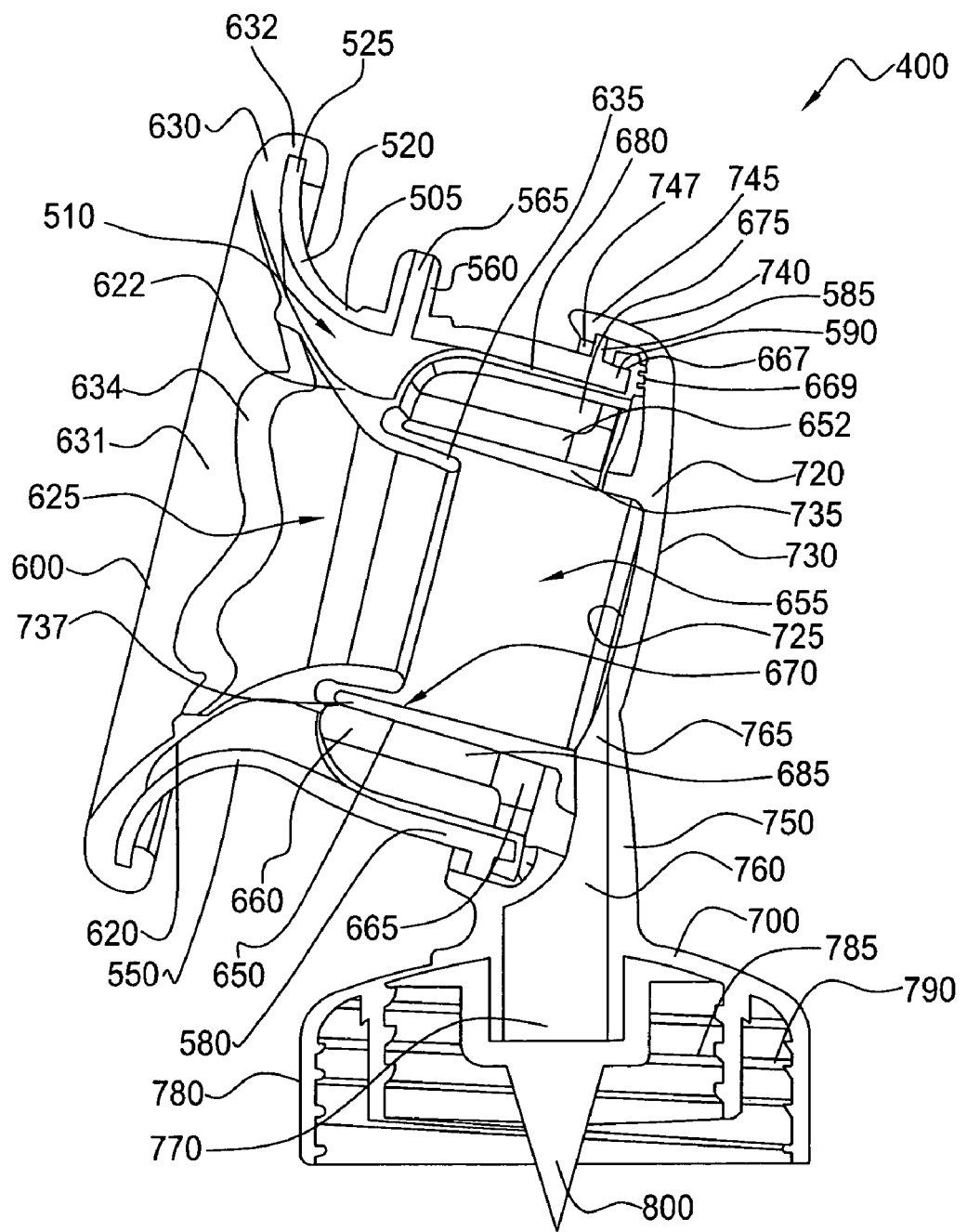
FIG. 7 is a side cross-sectional view of the breast cup of FIG. 1 taken along line 7-7 of FIG. 6.
Figure 8:
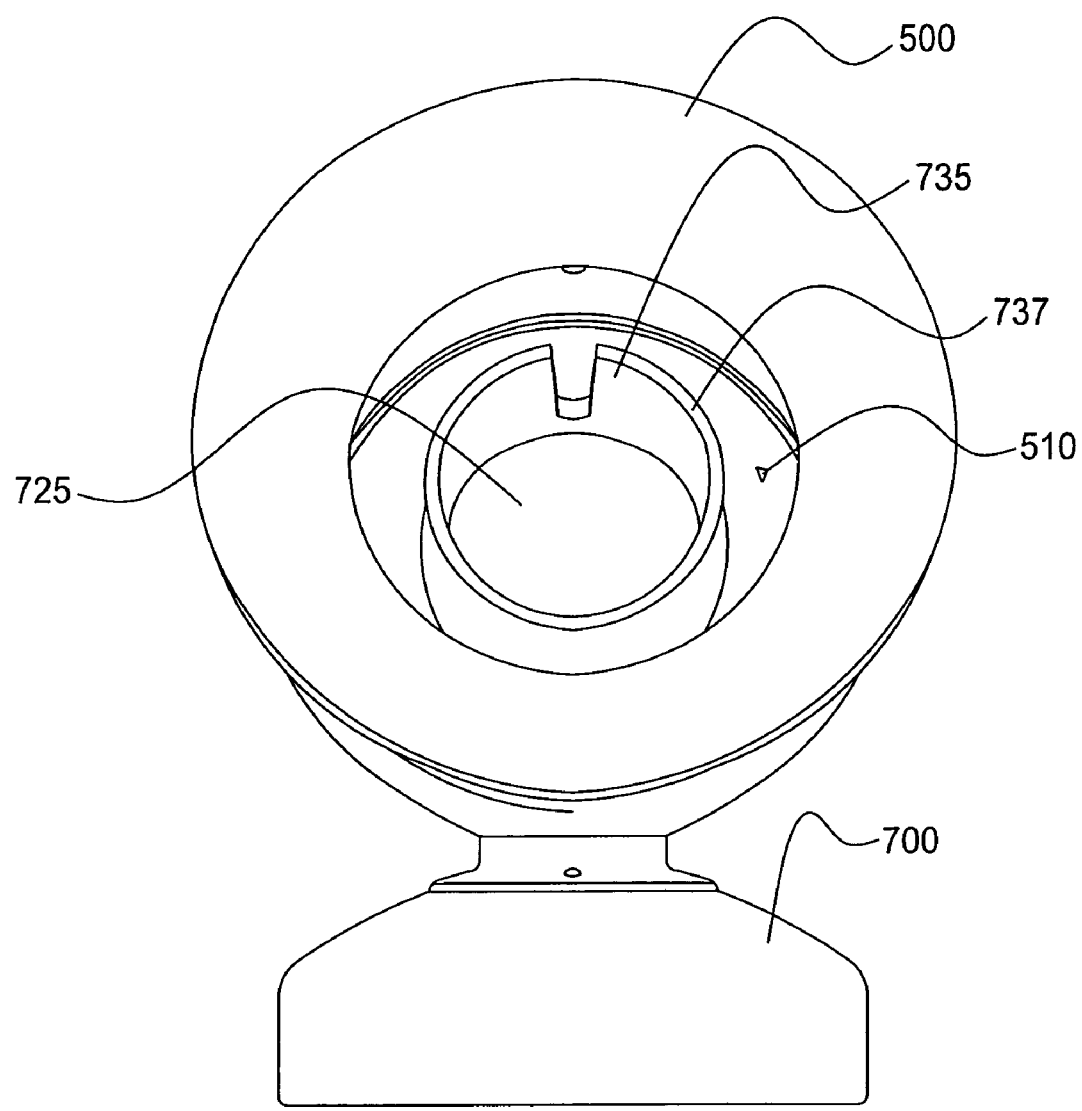
FIG. 8 is a front view of the housing and holder of FIG. 2.
Figure 9:
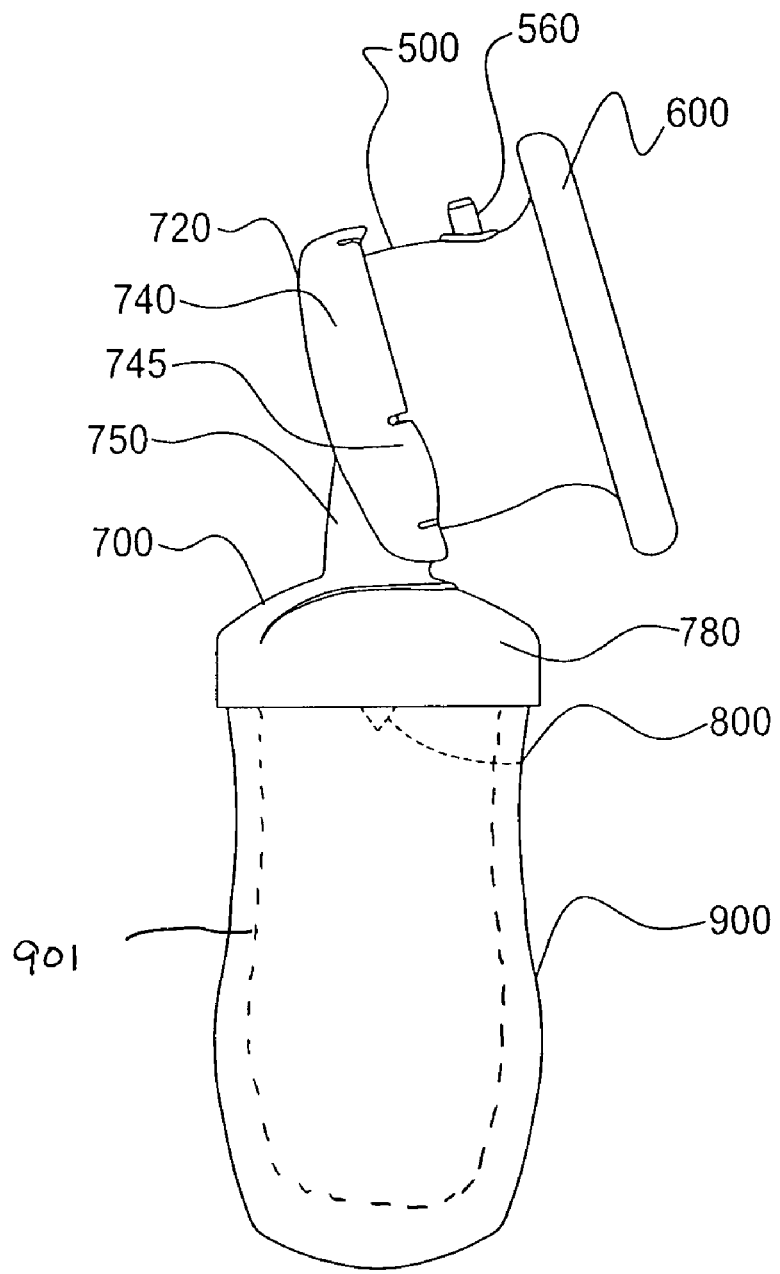
FIG. 9 is a side view of the breast cup of FIG. 1 with a bottle attached.

Referring in particular to FIG. 7, inner section 580 has a retaining ring 585 and an inner end 590. Retaining ring 585 is a circumferential ridge or ring extending outwardly from circumferential wall 505 and is adapted for engagement with holder 700. The use of a continuous circumferential ridge for retaining ring 585 allows a user to engage inner section 580 with holder 700 at any orientation or alignment to facilitate assembly. Alternative securing structures can also be used for retaining ring 585 such as, for example, a number of tongues formed along inner section 580 that engage with a corresponding number of grooves formed on holder 700.

Inner end 590 of inner section 580 is adapted for engagement with insert 600. Inner end 590 preferably has a generally uniform cross-section and uses a tongue and groove connection to engage with insert 600. This type of engagement between inner end 590 and insert 600 allows a user to engage the inner end with the insert at any orientation or alignment to facilitate assembly. However, alternative securing structures can also be used, such as, for example, a projection or number of projections formed on inner end 590 that engage with corresponding grooves or orifices formed in insert 600.

Insert 600 has a size and shape that generally corresponds to the size and shape of housing 500 to allow for assembly of the insert to the housing with sealing engagement of outer end 525 and inner end 590 of the housing with the insert. Insert 600 has an outer portion 620 and an inner portion 650. Outer portion 620 has a substantially conical shape with a first side wall 622 defining an outer volume 625. Outer portion 620 further has a first end 630 having an inner surface 631, and a second end 635. First side wall 622 converges or tapers towards inner portion 650.

Inner portion 650 has a substantially cylindrical shape with a second side wall 652 defining an inner volume 655. Inner portion 650 has a third end 660 and a fourth end 665. Preferably, outer portion 620 is integrally formed with inner portion 650 so that second end 635 of the outer portion is disposed within inner volume 655 and a circumferential gap or space 670 is provided between the second end of the outer portion and third end 660 of the inner portion.

First end 630 of outer portion 620 has an outer fastener 632 and a massaging member 634. In this embodiment, outer fastener 632 is a groove in first end 630 with a size and shape that corresponds to outer end 525 of housing 500 for a tongue and groove connection between the housing and insert 600. Preferably, first end 630 of insert 600 is curled over to form the groove for the tongue and groove connection. This connection provides for sealing engagement between housing 500 and insert 600 at first end 630 of the insert and further allows for connection of the housing and insert at any orientation or alignment.

Massaging member 634 is a projection or other change in the shape of insert 600 in the area of outer portion 620, which makes contact with or is in proximity to the user's areola region. Massaging member 634 provides the user with a massaging action on the areola region, which facilitates expression of breast milk. In this embodiment, massaging member 634 is a continuous ridge having a star-like or wave-like shape. Preferably, massaging member 634 is integrally formed with insert 600 along inner surface 631 of first end 630.

Alternative shapes and sizes of massaging member 634 can also be used. Additionally, massaging member 634 can be a number of ridges, either continuous or portioned, and can also be concentrically or eccentrically aligned. The positioning of massaging member 634 along inner surface 631 depends on the size and shape of the massaging member that is used. Massaging member 630 preferably is disposed along inner surface 631 so that the massaging member traverses the areola region of the user's breast when breast cup 400 is in use. In the preferred embodiment, the star-like or wave-like shape of massaging member 634 provides more contact area between the massaging member and areola region as opposed to a circular shape.

Inner portion 650 has a plurality of spacers 675 formed in second side wall 652. Preferably there are four spacers 675. Spacers 675 have an upper end 680 disposed adjacent to or in proximity with circumferential wall 505 of inner section 580 of housing 500. Spacers 675 and second side wall 652 form a number of bladders 685 having bladder volumes 687. Preferably, there are four bladders 685. Spacers 675 are preferably perpendicular to circumferential wall 505 of housing 500 and are barriers between the housing and insert 600 to provide additional structural integrity to inner portion 650 so that bladder volumes 687 do not fully collapse upon the housing. In one preferred embodiment, the plurality of spacers 675 is a plurality of folds or pleats formed in the circumferential wall 505 of housing 500.

As a result of the use of bladders 685, it has been found that a lower level of suction is required for expressing breast milk. This is an improvement over conventional breast cups that do not have bladders because in such a breast cup some of the suction force is used in stretching the flexible insert material. An additional advantage of the use of the bladder design is that bladders 685 prevent softer breasts from being sucked a substantial distance through outer and inner volumes 625, 655 which could impinge the pressurization of breast cup 400. Bladders 685 provide a barrier for softer breasts against impingement. While this embodiment uses folds or pleats 675 in second side wall 652 as a barrier between the second side wall and housing 500, alternative barriers can also be used, such as, for example, projections or solid walls extending from the second side wall to the housing.

Fourth end 665 of inner portion 650 has an inner fastener 667 and a sealing ring 669. In this embodiment, inner fastener 667 is a groove in fourth end 665 with a size and shape that corresponds to inner end 590 of housing 500 for a tongue and groove connection between the housing and insert 600. Preferably, fourth end 665 has a U-shape to form the groove for the tongue and groove connection. This connection provides for sealing engagement between housing 500 and insert 600 at fourth end 665 of the insert and further allows for connection of the housing and insert at any orientation or alignment. Sealing ring 669 is a circumferential ring or ridge preferably integrally formed with insert 600 that abuts against holder 700 when the insert and holder are assembled.

Insert 600 is made of a flexible material that is safe for contact with the breast milk. Such a flexible material is silicone. However, alternative flexible materials may also be used for flexible insert 600. When insert 600 is assembled to housing 500, the insert sealingly engages with the housing along outer end 525 and inner end 585 of the housing such that bladder volume 687 and that portion of housing volume 510 disposed between the insert and the housing, are in fluid communication with air orifice 560.

A breast pump (not shown) can be placed in fluid communication with breast cup 400 via air tubing or conduit that is connected to air orifice 560. An example of such a breast pump, as well as the components of such a system, is disclosed in the co-pending and commonly owned U.S. Application entitled "Breast Pump System" which has been filed evenly herewith, and the disclosure of which is incorporated herein by reference. The breast pump can supply both a positive and negative pressure to breast cup 400. While this embodiment of breast cup 400 can apply both a positive pressure and a negative pressure to a user's breast, alternatively, only a negative pressure or only a positive pressure may also be applied to the user's breast with use of the breast cup.

The positive and negative pressure created by the breast pump causes air to flow through air orifice 560 into and out of bladder volume 687 and housing volume 510. The positive and negative pressure supplied to breast cup 400 causes flexible insert 600 and, in particular, outer portion 620 and outer volume 625 to expand and contract to apply reciprocating positive and negative forces on the user's breast. The inflation and deflation of bladder volume 687 and housing volume 510 does not effect the longitudinal positioning of insert 600 in housing 500. The resulting movement of outer portion 620 of insert 600 causes massaging member 634 to apply a massaging force to the areola region of a user's breast.

Breast cup 400 is able to apply both a positive and negative pressure to a user's breast through a single air tubing which is connected to air orifice 560. Additionally, either an automatic or a manual breast pump can be connected to breast cup 400 via the air tubing to supply a positive pressure, a negative pressure or both.

The volume disposed between insert 600 and housing 500 that is in fluid communication with the breast pump, i.e., bladder volume 687 and that portion of housing volume 510 disposed between the insert and housing, is preferably between 22 to 52 cubic centimeters, and more preferably between 32 to 42 cubic centimeters. The expandable and contractible volume disposed between insert 600 and housing 500 also provides an upper limit to the amount of negative pressure that can be applied to a user's breast which can further serve as a safety limit for use of the breast pump. The sealing engagement of insert 600 and housing 500 provides a barrier between the user's breast and the vacuum source to prevent any breast milk from entering the air tubing or breast pump.

Referring to FIGS. 1 through 9, STET holder 700 has a back plate 720, a support rod 750 and a base 780. Back plate 720 has a circular shape with an inner surface 725, an outer surface 730 and a flange 740. Preferably, outer surface 730 is concave to facilitate gripping and holding of breast cup 400.

Inner surface 725 of back plate 720 has a barrier member 735 extending therefrom. Barrier member 735 has a distal end 737. Preferably, barrier member 735 has a substantially cylindrical shape and is perpendicular to back plate 720. When housing 500 and insert 600 are assembled to holder 700, distal end 737 of barrier member 735 is disposed in circumferential space 670 between outer portion 620 and inner portion 650 of the insert. Barrier member 735 is thus disposed substantially adjacent to bladders 685 and in inner volume 655 of insert 600. Barrier member 735 is a rigid barrier between inner volume 655 and bladders 685 to prevent the breast from making contact with and impinging the bladders, which would reduce the amount of their inflation and deflation and thus reduce the reciprocating pressure applied to the breast. Barrier member 735 especially provides a rigid barrier for softer breasts against such impingement, which are more likely to extend beyond outer volume 625 of insert 600 into inner volume 655. In one preferred embodiment, barrier member 735 is tubular.

Flange 740 is a circular wall that surrounds inner surface 725 and extends towards housing 500. Flange 740 has a diameter larger than the diameter of inner end 590 of housing 500 so that the inner end can be disposed within the flange and substantially abut against inner surface 725. Flange 740 has a number of securing tabs 745 formed therein. Securing tabs 745 are adapted for a snap fit engagement with retaining ring 585 of housing 500. Preferably, securing tabs 745 have detents 747 disposed on the distal end of the securing tab to facilitate the snap fit engagement. There are preferably three securing tabs 745. The use of a snap fit engagement between securing tabs 745 and continuous retaining ring 585, allows a user to assemble housing 500 to holder 700 in any orientation or alignment.

Support rod 750 connects back plate 720 to base 780. Preferably, support rod 750 is secured to back plate 720 so that the back plate is angled slightly from the vertical, i.e., back plate 720 leans backwards. Leaning back plate 720 backwards facilitates holding of breast cup 400 and applying the breast cup to the user's breast. Support rod 750 has a supply channel 760 formed therein. Supply channel 760 has an upper end 765 and a lower end 770. Upper end 765 is connected to back plate 720 and is in fluid communication with barrier member 735. Lower end 770 is connected to base 780 and is in fluid communication with the base.

Base 780 has a concave disk-like shape with an inner securing member 785 and an outer securing member 790. Inner securing member 785 is a first set of threads and outer securing member 790 is a second set of threads. The dual thread arrangement of securing members 785, 790 allows a user to attach base 780 to either standard reusable bottles or disposable liner holders (hereinafter "containers") which have differing diameters.

Valve 800 is a one-way valve that is sealingly engaged to lower end 770 of supply channel 760. One-way valve 800 allows the breast milk to flow into a container 900 that is secured to securing member 790 of base 780 or to allow the breast milk to flow into a second container 901 (shown in phantom) that is secured to securing member 785 of base 780, but prevents the negative pressure from sucking the milk out of the bottle. Preferably, valve 800 is a duck-bill valve. However, alternative one-way valves can also be used.

In operation, the expansion and contraction of insert 600 as described above, causes breast milk to be expressed from the user's breast. The breast milk flows through inner volume 655 of inner portion 650 of insert 600 and through barrier member 735 of holder 700. The breast milk then flows through supply channel 760 and into a bottle or a disposable liner with holder, which has been secured to base 780 of holder 800.

One of the advantages of breast cup 400 is the simplicity of assembly and cleaning. Breast cup 400 has only four components, i.e., housing 500, insert 600, holder 700 and valve 800. These components can be readily snap fitted together. Also, these components can be secured to each other under any orientation or alignment. Thus, a user does not have to spend time obtaining the correct alignment of the components prior to assembly. Further, the breast milk and air flow are sealingly separated by insert 600. Thus, breast milk cannot enter the air tubing and cannot enter the breast pump. This facilitates cleaning of the breast pump system.

Figure 10:
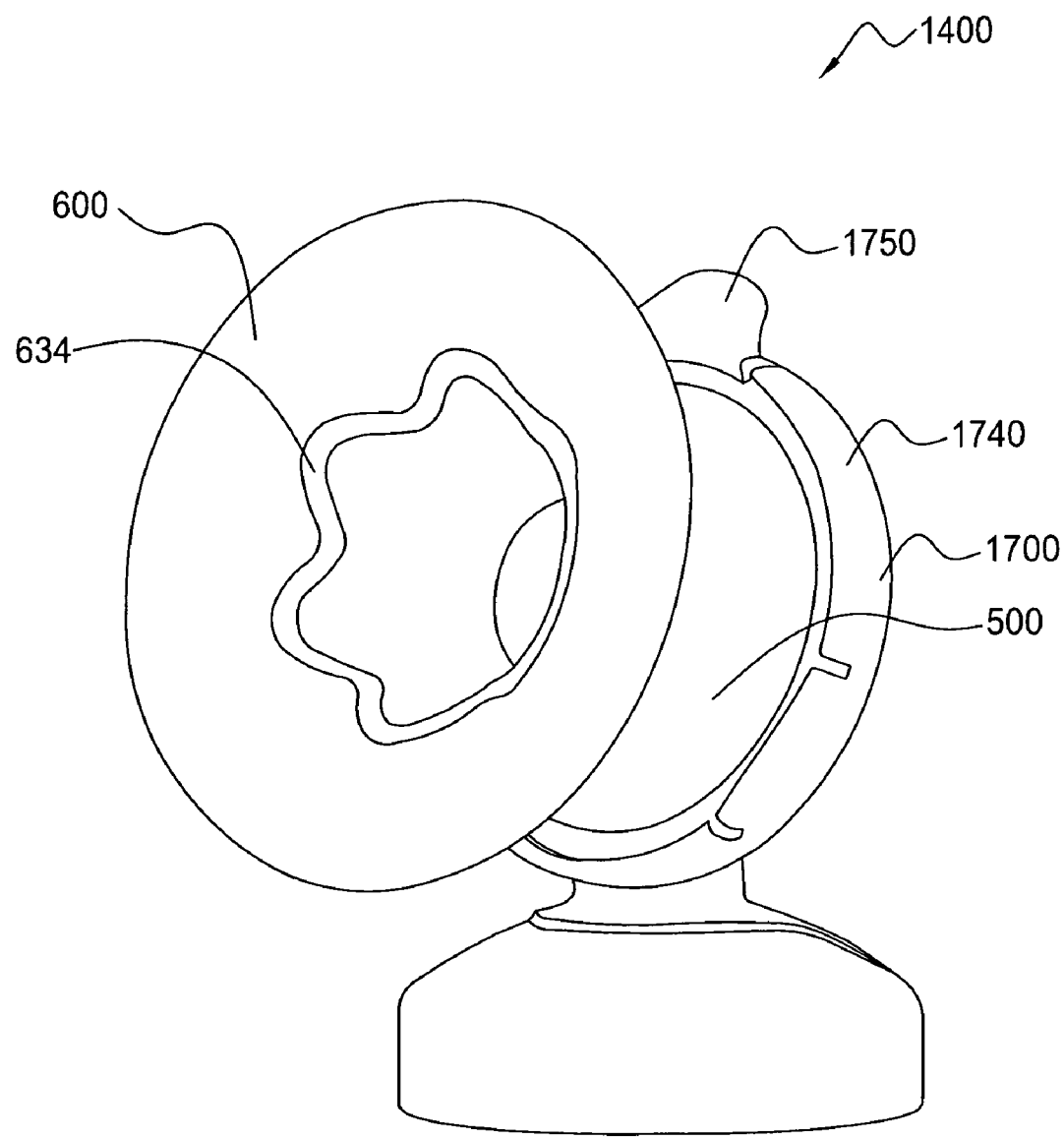
FIG. 10 is a front perspective view of an alternative embodiment of the breast cup of the present invention.
Figure 11:
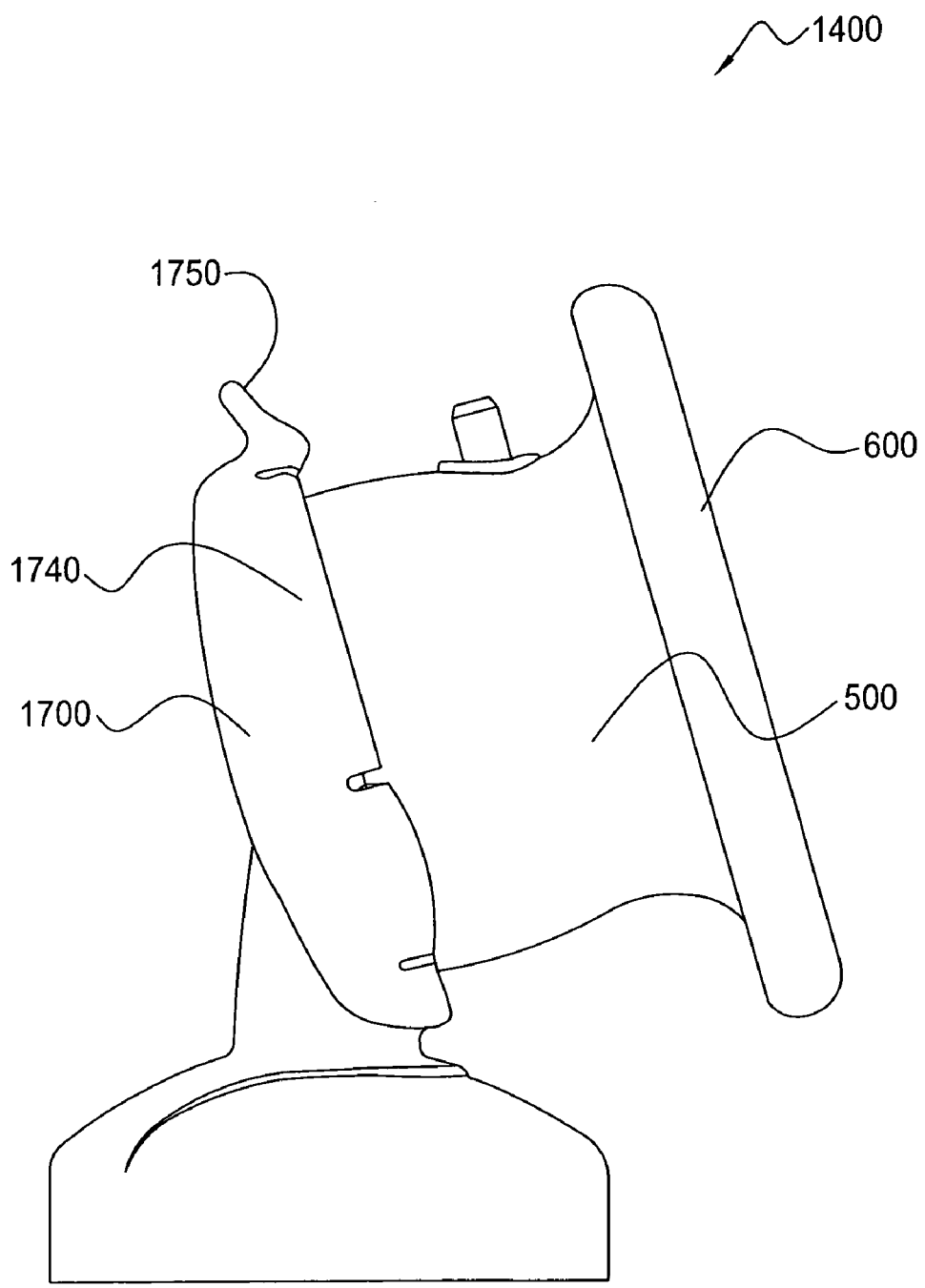
FIG. 11 is a side view of the breast cup of FIG. 10.

Referring to FIGS. 10 and 11, an alternative embodiment of the breast cup of the present invention is shown and generally represented by reference numeral 1400, with features that are similar to the features of breast cup 400 being represented by the same reference numerals. Breast cup 1400 has a housing 500, a flexible insert 600 and a holder 1700. Holder 1700 has features similar to holder 700 of the preferred embodiment but further includes a disassembly indicator 1750. Preferably, indicator 1750 is disposed along the top of holder 1700. More preferably, indicator 1750 is centrally disposed along the top of holder 1700 along flange 1740.

Indicator 1750 directs a user to those areas of housing 500 and holder 1700 that can be pivotally or rotationally moved for disassembly or disengagement of the housing and holder. Preferably, indicator 1750 directs a user to those areas of housing 500 and holder 1700, which can be more readily or easily disassembled or pulled apart. In this embodiment, indicator 1750 is a substantially flat, arcuate projection with a height and width that allows a user to place his or her finger on the indicator and pull or pivot housing 500 from engagement with holder 1700. The height of indicator 1750 provides leverage for pivotal or rotational movement of housing 500 relative to holder 1700 to facilitate disassembly or disengagement of these two parts.

Alternatively, indicator 1750 can have different shapes and sizes. Such shapes are preferably ergonomically designed to facilitate separation of housing 500 and holder 1700. Also, indicator 1750 can include other ways to direct a user to those areas of housing 500 and holder 1700 that can be disassembled or pulled apart, such as an arrow engraved in, or molded along, the top of the holder. Further, indicator 1750 can also be disposed in other areas of breast cup 1400, such as along the sides, and can be disposed on housing 500 rather than holder 1700.

Figure 12:
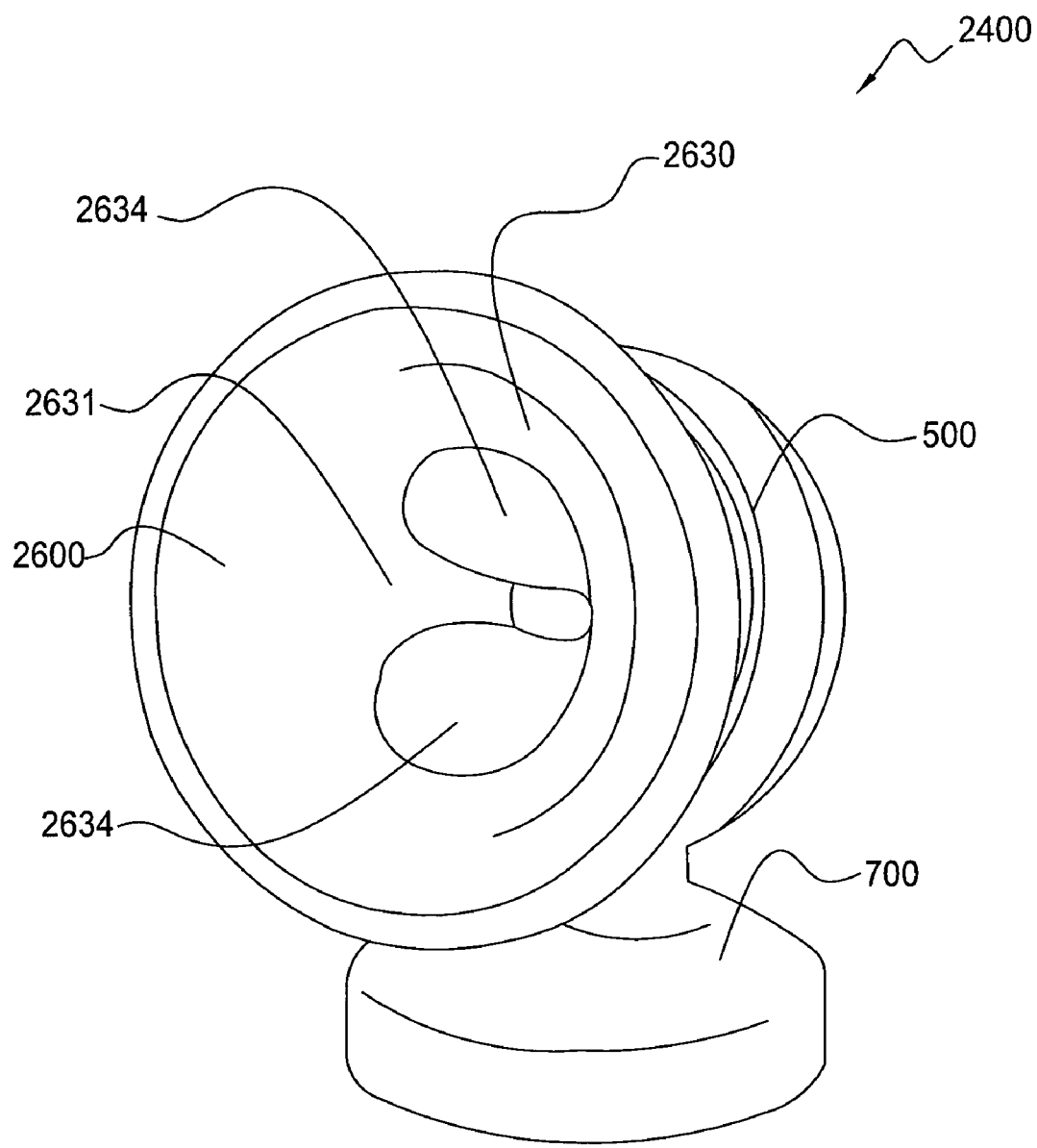
FIG. 12 is a front perspective view of another alternative embodiment of the breast cup of the present invention.

Referring to FIG. 12, an alternative embodiment of the breast cup of the present invention is shown and generally represented by reference numeral 2400, with features that are similar to the features of breast cup 400 being represented by the same reference numerals. Breast cup 2400 has a housing 500, a flexible insert 2600 and a holder 700. Flexible insert 2600 has features similar to insert 600 of the preferred embodiment except that an alternative massaging member 2634 is used. Massaging member 2634 is a pair of projections formed along inner surface 2631 of first end 2630 of insert 2600. Preferably, the pair of projections that form massaging member 2634 are disposed on opposing sides of first end 2630.

Figure 13:
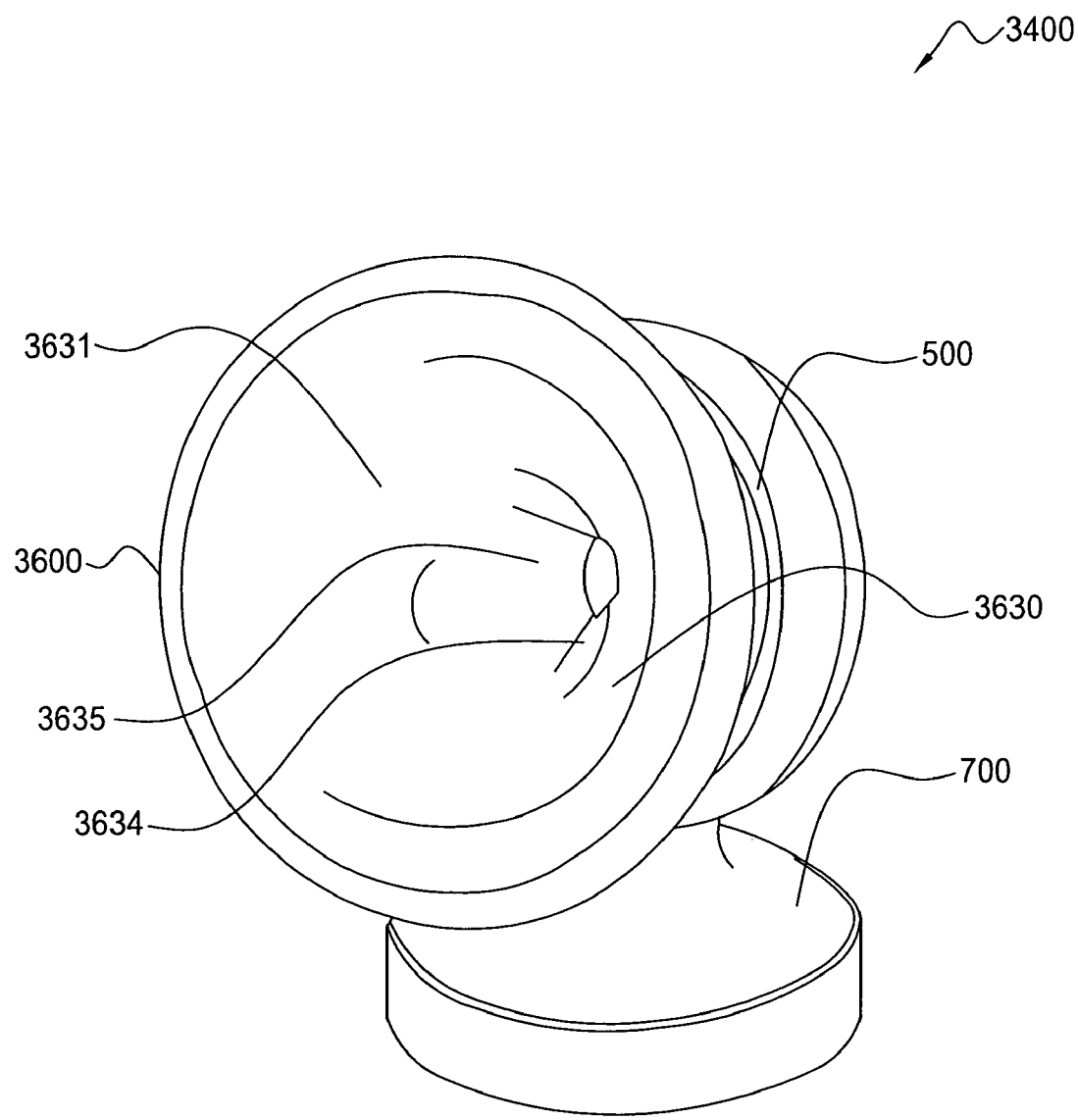
FIG. 13 is a front perspective view of another alternative embodiment of the breast cup of the present invention.

Referring to FIG. 13, an alternative embodiment of the breast cup of the present invention is shown and generally represented by reference numeral 3400, with features that are similar to the features of breast cup 400 being represented by the same reference numerals. Breast cup 3400 has a housing 500, a flexible insert 3600 and a holder 700. Flexible insert 3600 has features similar to insert 600 of the preferred embodiment except that an alternative massaging member 3634 is used. Massaging member 3634 is three projections formed along first end 3630 and second end 3635 of insert 3600. Preferably, the three projections that form massaging member 3634 are equally spaced apart.

Figure 14:
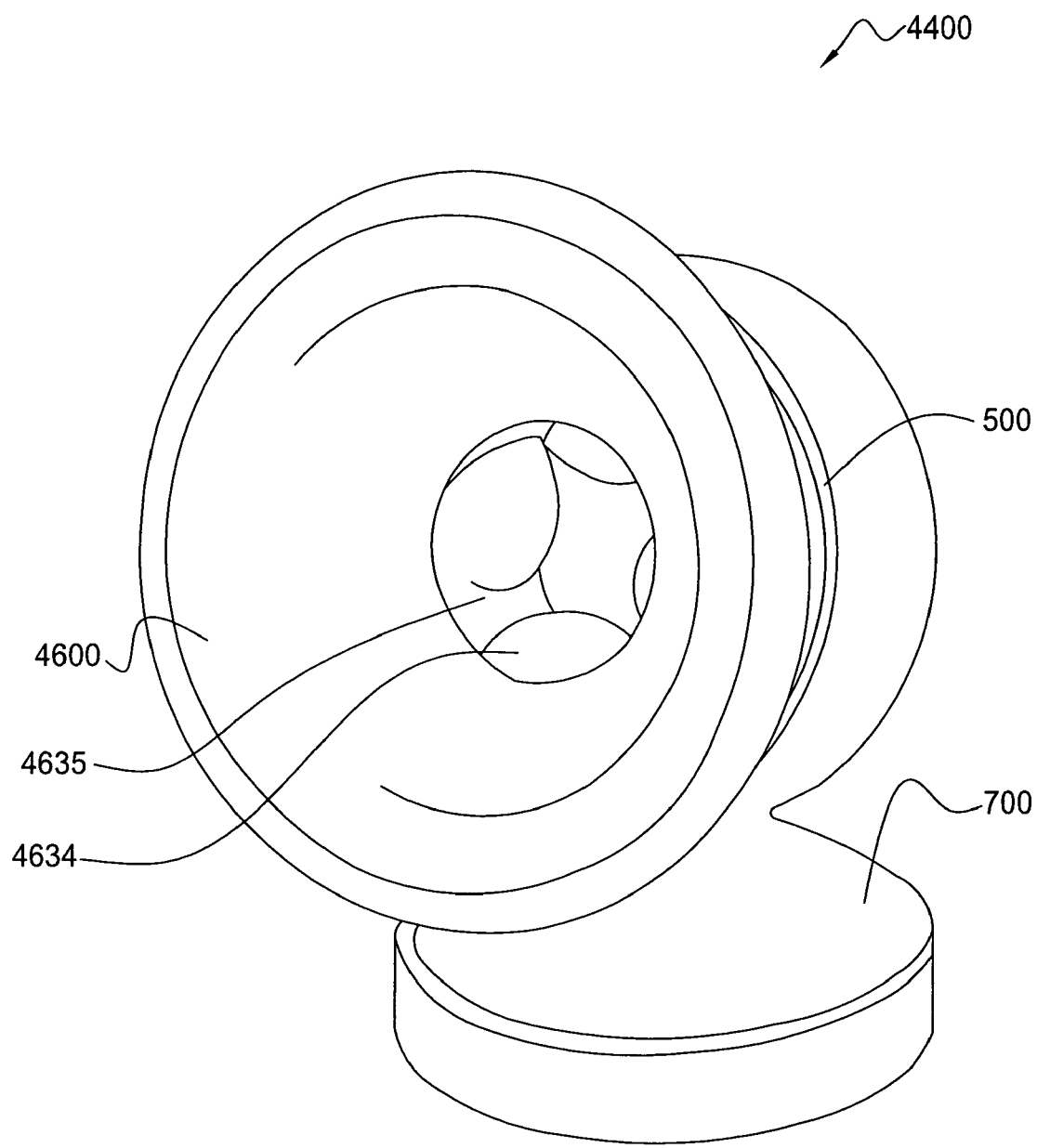
FIG. 14 is a front perspective view of another alternative embodiment of the breast cup of the present invention.

Referring to FIG. 14, an alternative embodiment of the breast cup of the present invention is shown and generally represented by reference numeral 4400, with features that are similar to the features of breast cup 400 being represented by the same reference numerals. Breast cup 4400 has a housing 500, a flexible insert 4600 and a holder 700. Flexible insert 4600 has features similar to insert 600 of the preferred embodiment except that an alternative massaging member 4634 is used. Massaging member 4634 is four projections formed along second end 4635 of insert 4600. Preferably, the four projections that form massaging member 4634 are equally spaced apart and diametrically opposed.

Figure 15:
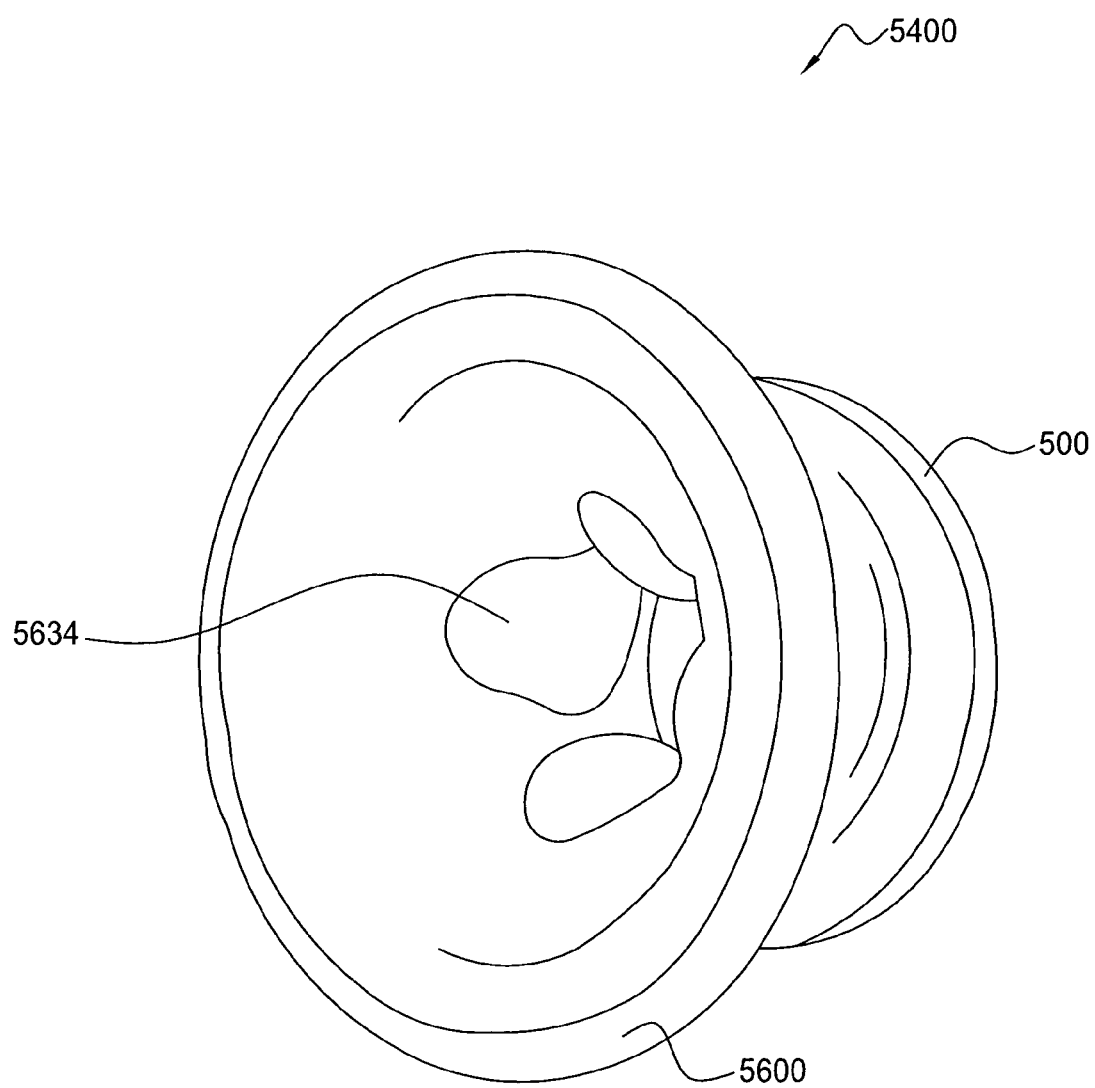
FIG. 15 is a front perspective view of another alternative embodiment of the breast cup of the present invention.
Figure 16:
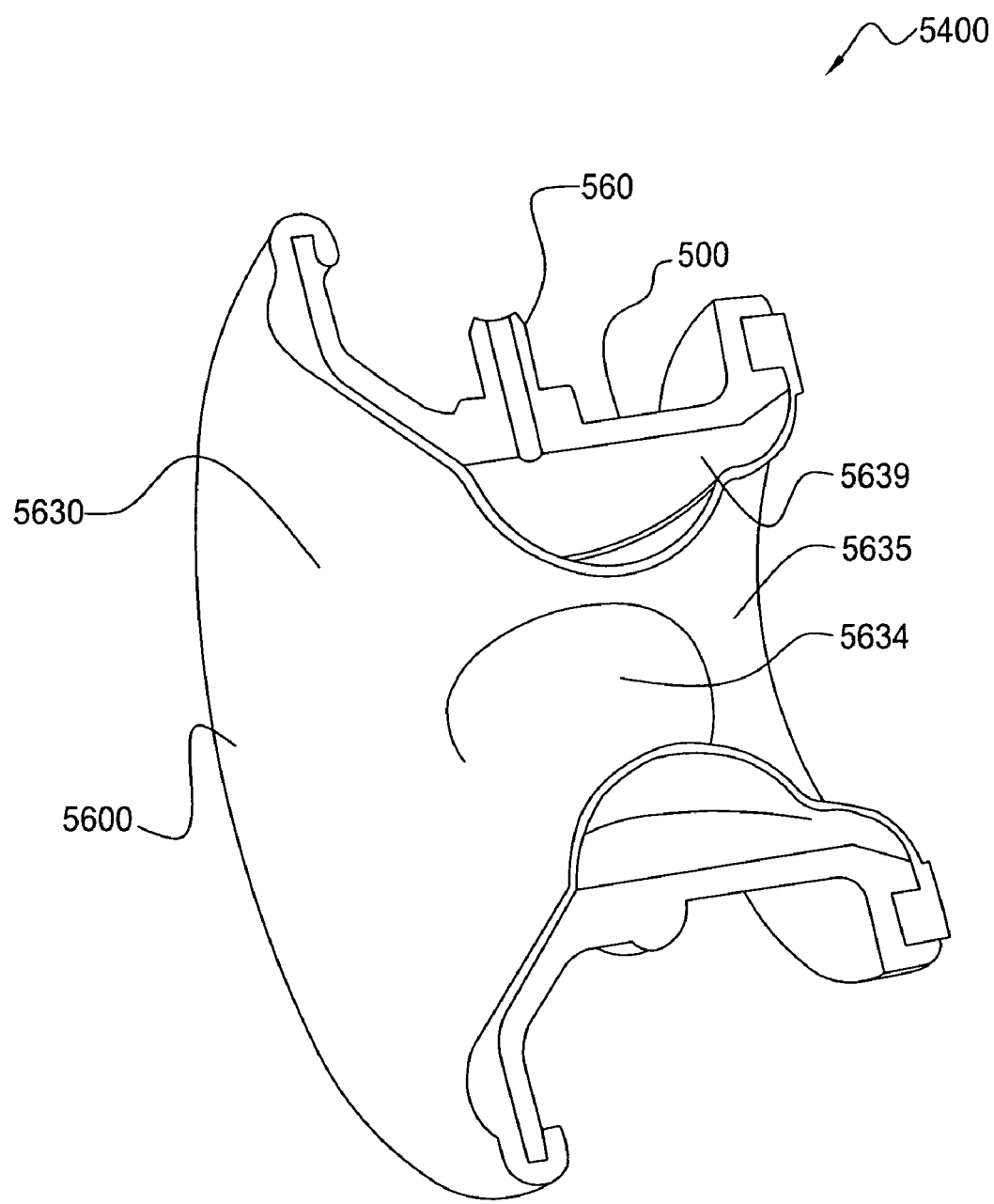
FIG. 16 is a front cross-sectional perspective view of the breast cup of FIG. 15.

Referring to FIGS. 15 and 16, an alternative embodiment of the breast cup of the present invention is shown and generally represented by reference numeral 5400, with features that are similar to the features of breast cup 400 being represented by the same reference numerals. Breast cup 5400 has a housing 500, a flexible insert 5600 and a holder 700 (not shown). Flexible insert 5600 has features similar to insert 600 of the preferred embodiment except that an alternative massaging member 5634 is used. Massaging member 5634 is four projections having a tear-drop shape and formed along first end 5630 and second end 5635 of insert 5600. Preferably, the four projections that form massaging member 5634 are equally spaced apart and diametrically opposed. As shown in FIG. 16, an inner volume 5639 of massaging member 5634 is in fluid communication with air orifice 560 so that the massaging members directly expand and contract.

Figure 17:
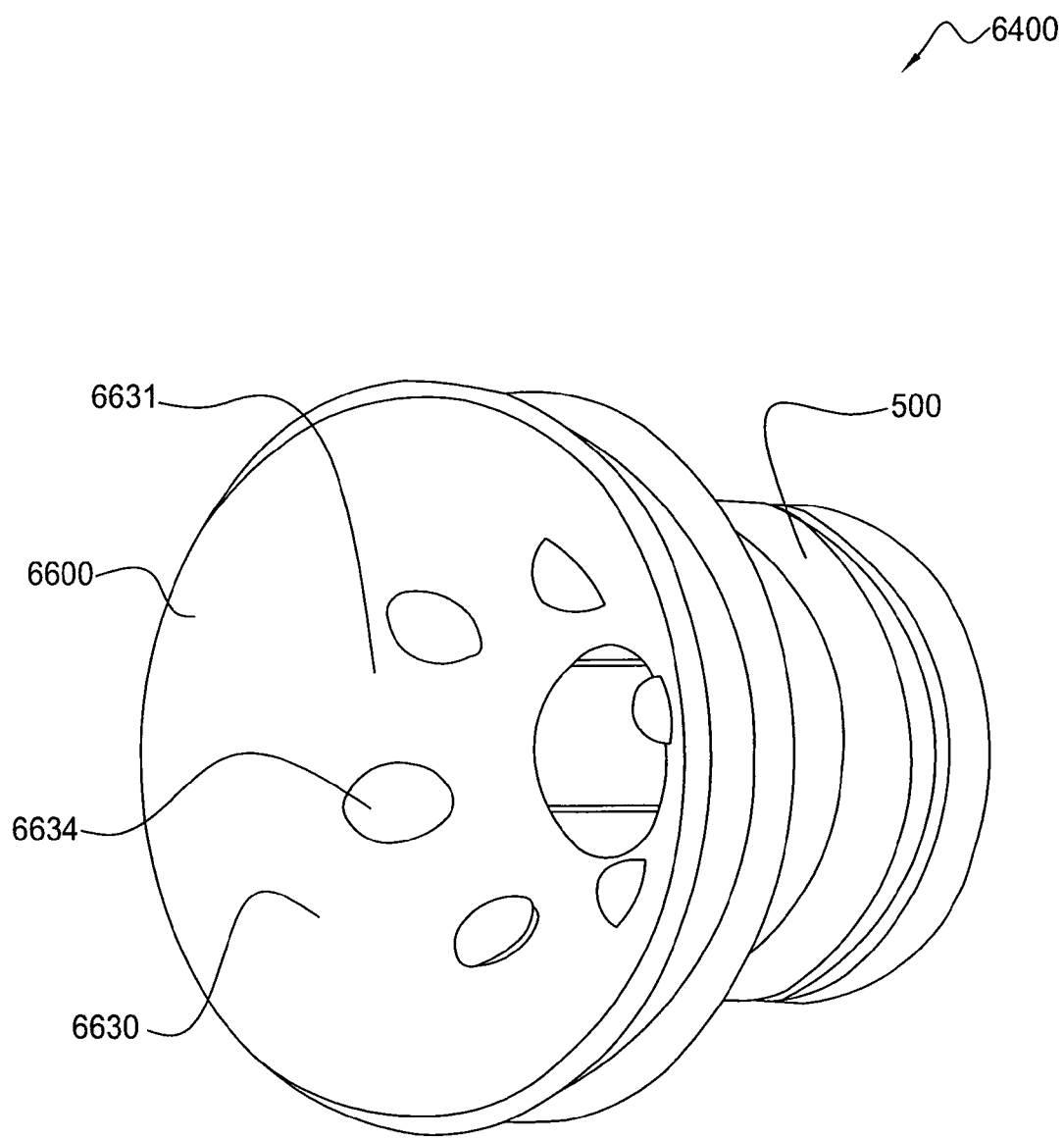
FIG. 17 is a front perspective view of another alternative embodiment of the breast cup of the present invention.
Figure 18:
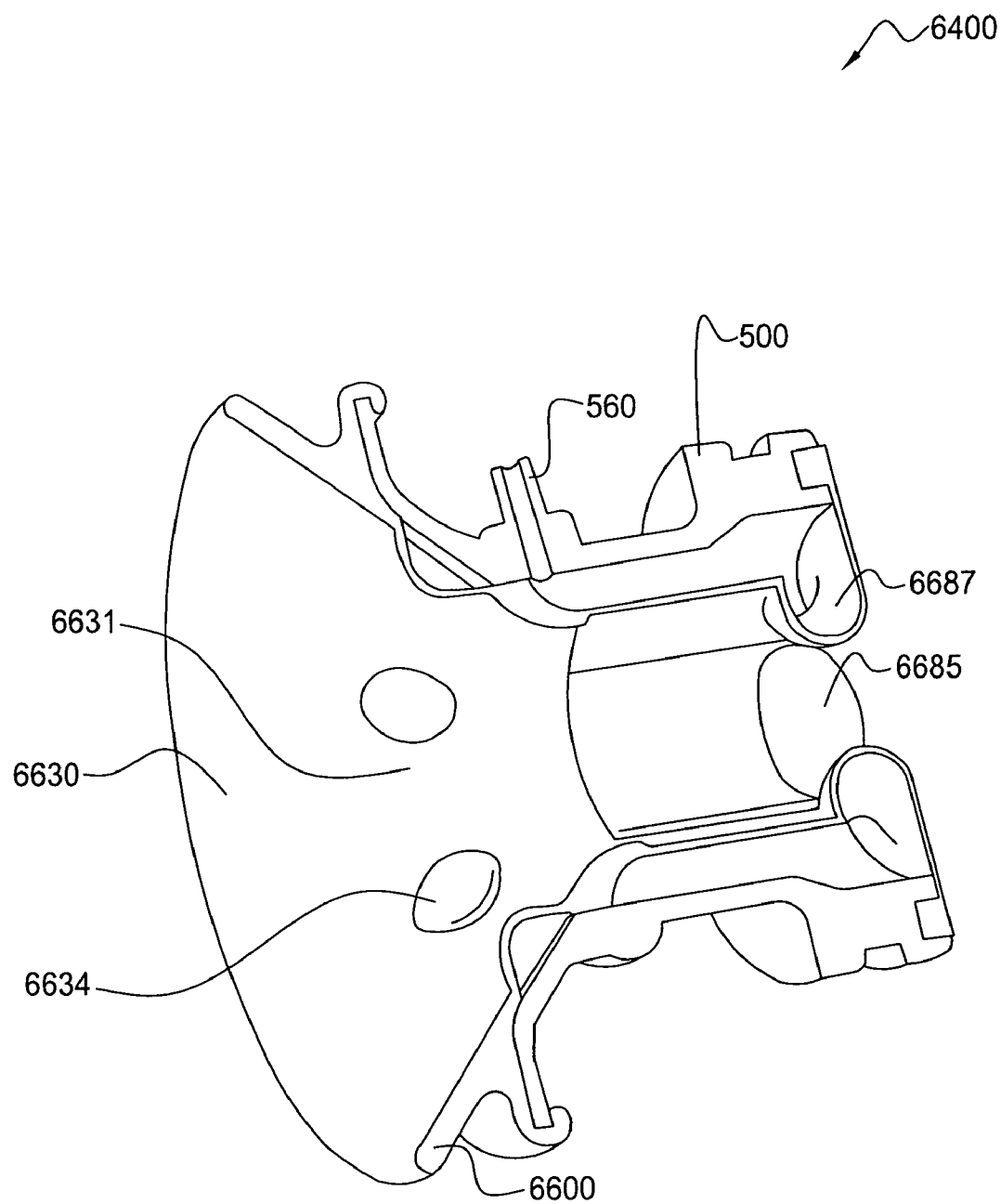
FIG. 18 is a front cross-sectional perspective view of the breast cup of FIG. 17.

Referring to FIGS. 17 and 18, an alternative embodiment of the breast cup of the present invention is shown and generally represented by reference numeral 6400, with features that are similar to the features of breast cup 400 being represented by the same reference numerals. Breast cup 6400 has a housing 500, a flexible insert 6600 and a holder 700 (not shown). Flexible insert 6600 has features similar to insert 600 of the preferred embodiment except that an alternative massaging member 6634 and bladders 6685 are used. Massaging member 6634 is six projections having a generally semi-spherical or elliptical shape, and formed along inner surface 6631 of first end 6630 of insert 6600. Preferably, the six projections that form massaging member 6634 are equally spaced apart and diametrically opposed. As shown in FIG. 18, a bladder volume 6687 of bladders 6685 is in fluid communication with air orifice 560 so that the bladders expand and contract to create a positive and negative pressure on the user's breast.

The present invention includes a number of components and is usable with a manual or motorized breast pump. The various components can be disposed within a bag system for ease of use. An example of such a bag system, as well as the components of such a system, is disclosed in the co-pending and commonly owned U.S. Application entitled "Bag System" which has been filed evenly herewith, and the disclosure of which is incorporated herein by reference.

The present invention having been thus described with particular reference to the preferred forms thereof, it will be obvious that various changes and modifications may be made therein without departing from the spirit and scope of the present invention as defined in the appended claims.

What is claimed is:

1. A breast cup for the expression of breast milk from a breast having an areola region, using pressure, the breast cup comprising:
    a housing having an air orifice;
    a flexible insert defining a liquid volume for receiving a portion of the breast and being sealingly secured to said housing to form an air volume therebetween; and
    a barrier member which is rigid, wherein said air orifice is in fluid communication with said air volume and in fluid isolation with said liquid volume, said air volume and said liquid volume are in fluid isolation, and said air volume expands or contracts in response to said pressure and wherein said barrier member is substantially adjacent to a portion of said air volume thereby preventing the breast from contacting said flexible insert along said portion of said air volume.

2. The breast cup of claim 1, further comprising a holder being securable to said housing, wherein said housing, said flexible insert and said holder are securable to each other at a plurality of orientations.

3. The breast cup of claim 2, wherein said holder is secured to said housing by a snap fit connection.

4. The breast cup of claim 2, further comprising first and second containers, wherein said first container has a first diameter and said second container has a second diameter, wherein said holder has a first securing structure and a second securing structure, and wherein said first securing structure is removably securable to said first container and said second securing structure is removably securable to said second container.

5. The breast cup of claim 4, wherein said first securing structure is a first threaded surface having a first inner diameter and said second securing structure is a second threaded surface having a second inner diameter.

6. The breast cup of claim 5, wherein said first threaded surface and said second threaded surface are concentrically disposed on said holder.

7. The breast cup of claim 2, further comprising a one-way valve, wherein said holder has a channel that is in fluid communication with said liquid volume, and said one-way valve is operably connected to said channel.

8. The breast cup of claim 1, wherein said flexible insert comprises a bladder and said air volume is disposed at least partially in said bladder, wherein said bladder expands or contracts in response to said pressure.

9. The breast cup of claim 8, wherein said barrier member is disposed substantially adjacent to said bladder, said barrier member preventing said breast from contacting at least a portion of said bladder.

10. The breast cup of claim 9, wherein said barrier member has a cylindrical shape and is disposed in said liquid volume.

11. The breast cup of claim 10, further comprising a holder being securable to said housing, wherein said barrier member is directly connected to said holder and substantially concentrically aligned with said liquid volume.

12. The breast cup of claim 1, wherein said flexible insert has a funnel shape with a first portion that at least partially defines said air volume, said first portion has a massaging projection formed therein, and said massaging projection is disposed along said first portion to be in proximity to the areola region of the breast.

13. The breast cup of claim 12, wherein said massaging projection comprises a continuous ridge having a star-like shape.

14. The breast cup of claim 12, wherein the pressure is a positive pressure and a negative pressure, wherein said flexible insert further comprises a substantially cylindrical second portion having a circumferential wall and a plurality of spacers formed in said circumferential wall, said circumferential wall being separated from said housing by said plurality of spacers, and said circumferential wall and said plurality of spacers at least partially defining said air volume, wherein said circumferential wall is moved in proximity to said housing by said negative pressure and said circumferential wall is moved remote from said housing by said positive pressure.

15. The breast cup of claim 14, wherein said plurality of spacers are a plurality of pleats formed in said circumferential wall.

16. The breast cup of claim 1, wherein said housing has an outer end and an inner end, said flexible insert has an outer portion with a first end and an inner portion with a fourth end, said first end being removably secured to said outer end by a first securing structure, and said fourth end being removably secured to said inner end by a second securing structure.

17. The breast cup of claim 16, wherein said first securing structure and said second securing structure are tongue and groove securing structures.

18. The breast cup of claim 1, wherein the pressure is a positive pressure and a negative pressure, and wherein said air volume expands in response to said positive pressure and contracts in response to said negative pressure.

19. A breast cup for the expression of breast milk from a breast having an areola region, using pressure, the breast cup comprising:
   a housing having an air orifice;
   a flexible insert comprising a bladder and having a plurality of spacers and defining a liquid volume, wherein said bladder is defined in part by one or more of said plurality of spacers, said flexible insert being sealingly secured to and received in said housing to form an air volume therebetween, and wherein said air volume is disposed at least partially in said bladder, and wherein said bladder moves in response to said pressure;
   a barrier member disposed substantially adjacent to said bladder, said barrier member preventing said breast from contacting at least a portion of said bladder;
   a holder having a one-way valve, said holder being secured to said housing; and
   a container being secured to said holder, wherein said air orifice is in fluid communication with said air volume and in fluid isolation with said liquid volume, said air volume and said liquid volume are in fluid isolation, and said pressure is applied to said air volume causing said flexible insert to move with respect to said housing, wherein said liquid volume is in fluid communication with said container, and wherein each of said plurality of spacers extends toward said housing and substantially traverses said air volume along a length of said housing.

20. The breast cup of claim 19, wherein said housing, said flexible insert and said holder are securable to each other at a plurality of orientations.

21. The breast cup of claim 19, wherein said holder is secured to said housing by a snap fit connection.

22. The breast cup of claim 19, wherein said holder has a channel that is in fluid communication with said liquid volume and said container, and said one-way valve is operably connected to said channel.

23. The breast cup of claim 19 wherein said barrier member has a cylindrical shape and is disposed in said liquid volume.

24. The breast cup of claim 23, wherein said barrier member is secured to said holder and substantially concentrically aligned with said liquid volume.

25. The breast cup of claim 19, wherein said flexible insert has a funnel shape with a first portion that at least partially defines said air volume, said first portion has a massaging projection formed therein, and said massaging projection is disposed along said first portion to be in proximity to said areola region of said breast.

26. The breast cup of claim 25, wherein said massaging projection is a continuous ridge having a wave-like shape.

27. The breast cup of claim 26, wherein said flexible insert comprises first and second portions, said first portion being upstream from said second portion, and wherein said plurality of spacers are disposed in said second portion.

28. The breast cup of claim 27, wherein said plurality of spacers are a plurality of pleats formed in a circumferential wall of said flexible insert.

29. The breast cup of claim 19, wherein said housing has an outer end and an inner end, said insert has an outer portion with a first end and an inner portion with a fourth end, said first end being removably secured to said outer end by a first securing structure, and said fourth end being removably secured to said inner end by a second securing structure.

30. The breast cup of claim 29, wherein said first securing structure and said second securing structure are tongue and groove securing structures.

31. A breast cup for the expression of breast milk from a breast having an areola region, using pressure, the breast cup comprising:
   a housing having an air orifice;
   a flexible insert comprising a bladder and defining a liquid volume comprising a circumferential wall and a plurality of spacers, said flexible insert being sealingly secured to and received in said housing to form an air volume therebetween and wherein each of said plurality of spacers extends radially into the air volume to separate said housing from the circumferential wall;
   a barrier member disposed substantially adjacent to said bladder, said barrier member preventing said breast from contacting at least a portion of said bladder;
   a holder having a one-way valve, said holder being secured to said housing; and
   a container being secured to said holder for collecting expressed breast milk, wherein said air orifice is in fluid communication with said air volume and in fluid isolation with said liquid volume, said air volume and said liquid volume are in fluid isolation, and said pressure is applied to said air volume causing said flexible insert to move with respect to said housing, wherein said liquid volume is in fluid communication with said container, wherein said container is a first container having a first diameter and a second container having a second diameter, wherein said holder has a first securing structure and a second securing structure, and wherein said first securing structure is removably securable to said first container and said second securing structure is removably securable to said second container.

32. The breast cup of claim 31, wherein said first securing structure is a first threaded surface having a first inner diameter and said second securing structure is a second threaded surface having a second inner diameter.

33. The breast cup of claim 32, wherein said first threaded surface and said second threaded are concentrically disposed on said holder.

34. A breast hood for expression of breast milk from a breast having an areola region, in response to a pressure from a pressure source, the breast hood comprising:
   a rigid structure having a funnel shape;
   a flexible structure being sealingly secured to and received in said rigid structure, said flexible structure receiving a portion of the breast;
   a displacement volume disposed between said rigid structure and said flexible structure;
   a liquid volume defined along a longitudinal axis of said flexible structure, said liquid volume being in fluid isolation from said pressure source;
   a channel in fluid communication with said pressure source and said displacement volume; and
   a barrier member which is more rigid than said flexible structure, wherein said pressure source changes the pressure in said displacement volume, and wherein said barrier member has at least a portion thereof that is disposed in said liquid volume thereby preventing the breast from contacting at least a portion of said flexible structure.

35. The breast hood of claim 34, wherein said flexible structure comprises a bladder and said displacement volume is disposed at least partially in said bladder, wherein said bladder moves in response to a change in pressure in said displacement volume.

36. The breast hood of claim 35, wherein said barrier member is disposed substantially adjacent to said bladder, said barrier member preventing said breast from contacting at least a portion of said bladder.

37. The breast hood of claim 36, wherein said barrier member has a cylindrical shape and is disposed in said liquid volume.

38. The breast hood of claim 34, wherein said flexible structure has a first portion with a funnel shape that at least partially defines said displacement volume, said first portion having a massaging projection formed therein, and said massaging projection being disposed along said first portion to be in proximity to the areola region of the breast.

39. The breast hood of claim 38, wherein said massaging projection has a star-like shape.

40. The breast hood of claim 38, wherein said flexible structure further comprises a second portion having a circumferential wall and a plurality of spacers formed in said circumferential wall, said circumferential wall being separated from said rigid structure by said plurality of spacers, and said circumferential wall and said plurality of spacers at least partially defining said displacement volume, wherein said circumferential wall is moved in relation to said rigid structure by said change in pressure in said displacement volume.

41. The breast hood of claim 40, wherein said plurality of spacers are a plurality of pleats formed in said circumferential wall.

42. The breast hood of claim 34, wherein said housing has an outer end and an inner end, said insert has an outer portion with a first end and an inner portion with a fourth end, said first end being removably secured to said outer end by a first securing structure, and said fourth end being removably secured to said inner end by a second securing structure.

43. The breast hood of claim 42, wherein said first securing structure and said second securing structure are tongue and groove securing structures.

* * * * *